US008939956B2

(12) United States Patent
Mukai et al.

(10) Patent No.: US 8,939,956 B2
(45) Date of Patent: Jan. 27, 2015

(54) WEARING ARTICLE

(75) Inventors: Hirotomo Mukai, Kanonji (JP); Takaya Arayama, Kanonji (JP)

(73) Assignee: Unicharm Corporation, Ehime-Ken (JP)

( * ) Notice: Subject to any disclaimer, the term of this patent is extended or adjusted under 35 U.S.C. 154(b) by 274 days.

(21) Appl. No.: 13/641,914

(22) PCT Filed: Apr. 19, 2011

(86) PCT No.: PCT/JP2011/059666
§ 371 (c)(1),
(2), (4) Date: Jan. 18, 2013

(87) PCT Pub. No.: WO2011/132688
PCT Pub. Date: Oct. 27, 2011

(65) Prior Publication Data
US 2013/0110075 A1    May 2, 2013

(30) Foreign Application Priority Data

Apr. 19, 2010    (JP) ................................ 2010-096538

(51) Int. Cl.
*A61F 13/15*    (2006.01)
*A61F 13/49*    (2006.01)
*A61F 13/494*    (2006.01)

(52) U.S. Cl.
CPC . *A61F 13/49017* (2013.01); *A61F 2013/49034* (2013.01); *A61F 2013/49026* (2013.01);
(Continued)

(58) Field of Classification Search
CPC .................... A61F 13/49017; A61F 13/49019; A61F 2013/49025; A61F 2013/49026; A61F 2013/49034; A61F 2013/49036; A61F 2013/49042

USPC ......................................... 604/385.24, 385.25
See application file for complete search history.

(56) References Cited

U.S. PATENT DOCUMENTS 4,935,021 A * 6/1990 Huffman et al. .......... 604/385.26
5,593,400 A * 1/1997 O'Leary .................. 604/385.27
(Continued)

FOREIGN PATENT DOCUMENTS

EP         1875819 A1    1/2008
JP      2004329590 A    11/2004
(Continued)

OTHER PUBLICATIONS

International Search Report and Written Opinion corresponding to PCT/JP2011/059666, dated Jul. 12, 2011.
(Continued)

*Primary Examiner* — Lynne Anderson
(74) *Attorney, Agent, or Firm* — Lowe Hauptman & Ham LLP

(57) ABSTRACT

A wearing article includes a chassis and an absorber main body. The wearing article has a central elastic member overlapping a non-skin surface of an absorber in the crotch region and extending along a longitudinal direction at an approximately center of a widthwise direction of the wearing article, and a back leg elastic member that curves within the crotch region from the end of a back waistline region in the widthwise direction and configures at least a part of an elastic stress line that crosses the absorber along the widthwise direction. In the elastic stress line, the elastic stress of the portion crossing the absorber is smaller than the elastic stress of the central elastic member.

11 Claims, 15 Drawing Sheets

(52) U.S. Cl.
CPC . *A61F13/49019* (2013.01); *A61F 2013/49025* (2013.01); *A61F 13/49011* (2013.01); *A61F 13/494* (2013.01)
USPC .................................................. 604/385.24

(56) References Cited

U.S. PATENT DOCUMENTS

| | | | | |
|---|---|---|---|---|
| 5,634,917 | A * | 6/1997 | Fujioka et al. | 604/385.29 |
| 6,454,750 | B1 * | 9/2002 | Vogt et al. | 604/385.19 |
| 2001/0007936 | A1 * | 7/2001 | Shimoe et al. | 604/385.24 |
| 2002/0007172 | A1 * | 1/2002 | Takei et al. | 604/385.27 |
| 2003/0040732 | A1 * | 2/2003 | Ishikawa et al. | 604/385.29 |
| 2006/0161131 | A1 * | 7/2006 | Kurata et al. | 604/385.28 |
| 2008/0027406 | A1 | 1/2008 | Shirai et al. | |
| 2009/0312739 | A1 | 12/2009 | Umebayahi et al. | |

FOREIGN PATENT DOCUMENTS

| | | |
|---|---|---|
| JP | 2006122396 A | 5/2006 |
| JP | 2006149747 A1 | 6/2006 |
| JP | 2007167166 A | 7/2007 |
| JP | 2007167166 A1 | 7/2007 |
| JP | 2007195738 A1 | 8/2007 |
| WO | 2006118214 A1 | 11/2006 |

OTHER PUBLICATIONS

Extended European Search Report issued Jan. 17, 2014, corresponds to European patent application No. 11772021.9.
First Notification of Reasons for Refusal dated Feb. 24, 2014, in corresponding Chinese Patent Application No. 201180019772.4, and English language translation thereof.

* cited by examiner

WEARING ARTICLE

RELATED APPLICATIONS

The present application is a National Phase of International Application Number PCT/JP2011/059666, filed Apr. 19, 2011, and claims priority from Japanese Application Number 2010-096538, filed Apr. 19, 2010.

TECHNICAL FIELD

The present disclosure relates to a wearing article comprising a chassis and an absorber main body. The wearing article may be a pants-type diaper for use by infants or adults. In particular, the wearing article may be a pants-type diaper for adult incontinence.

BACKGROUND ART

A wearing article, such as a pant-type diaper has a chassis and an absorber main body. The chassis includes a front waistline region, a back waistline region, and a crotch region. Here, the chassis includes an elastic member, such as rubber for attaching the wearing article tightly to the skin of the wearer.

The elastic member, for example, is a leg hole elastic body for attaching the wearing article tightly around the leg of the wearer, or a crotch elastic body for attaching the wearing article tightly to the crotch of the wearer (for example, Patent Document 1).

PRIOR ART DOCUMENT

Patent Document

[Patent Document 1]
Japanese Unexamined Patent Application Publication No. 2007-167166

SUMMARY OF INVENTION

Problem(s) to be Solved by Invention

In relation to wearing articles for incontinence, there are cases where the urine flow is slow and cases where the amount of urine is large. In the case when the urine flow is slow, there is a possibility of leakage outside the wearing article along the skin of the wearer. Therefore, it is important to have high contact between the excretion portion (excretion region) of the wearer and the absorber main body. On the other hand, in the case where the amount of urine discharged is large, there is a possibility of leakage outside the wearing article due to the inability of the absorber main body to absorb the urine instantaneously.

Thus, the present invention helps to resolve the above problems and its purpose is to provide a wearing article that enables prevention of leakage of urine outside the wearing article in the cases of both slow urine flow and discharge of a large amount of urine.

Means for Solving the Invention

A wearing article according to a first aspect of the present invention comprises a chassis, which has a waistline region and a crotch region, and an absorber main body, which has an absorber provided in at least the crotch region of the chassis, the wearing article further comprising: a first elastic member overlapping a non-skin-facing surface of the absorber in the crotch region and extending along a longitudinal direction of the wearing article at an approximate center of a widthwise direction of the wearing article; a second elastic member which curves within the crotch region from both ends of the waistline region in the widthwise direction of the wearing article; and an elastic stress line which crosses the absorber along the widthwise direction of the wearing article; wherein the second elastic member forms at least a part of the elastic stress line; and wherein, in the elastic stress line, the elastic stress of the portion crossing the absorber is smaller than the elastic stress of the first elastic member.

A wearing article according to a second aspect of the present invention comprises a chassis, which has a waistline region and a crotch region, and an absorber main body, which has an absorber provided in at least the crotch region of the chassis, the wearing article further comprising: a first elastic member overlapping the absorber in the crotch region and extending along a longitudinal direction of the wearing article at an approximate center of a widthwise direction of the wearing article; wherein the first elastic member comprises a portion arranged to be directly under the crotch of a wearer in use and provided at an approximate center of the wearing article in the longitudinal direction of the wearing article; wherein the first elastic member further comprises an extending portion which continues in succession to the portion arranged to be directly under the crotch in the longitudinal direction of the wearing article; and wherein the elastic stress of the extending portion is smaller than the elastic stress of the portion arranged to be directly under the crotch. The second aspect of the present invention may be independent of or dependent on the first aspect of the present invention.

DESCRIPTION OF EMBODIMENTS

Figure 1:
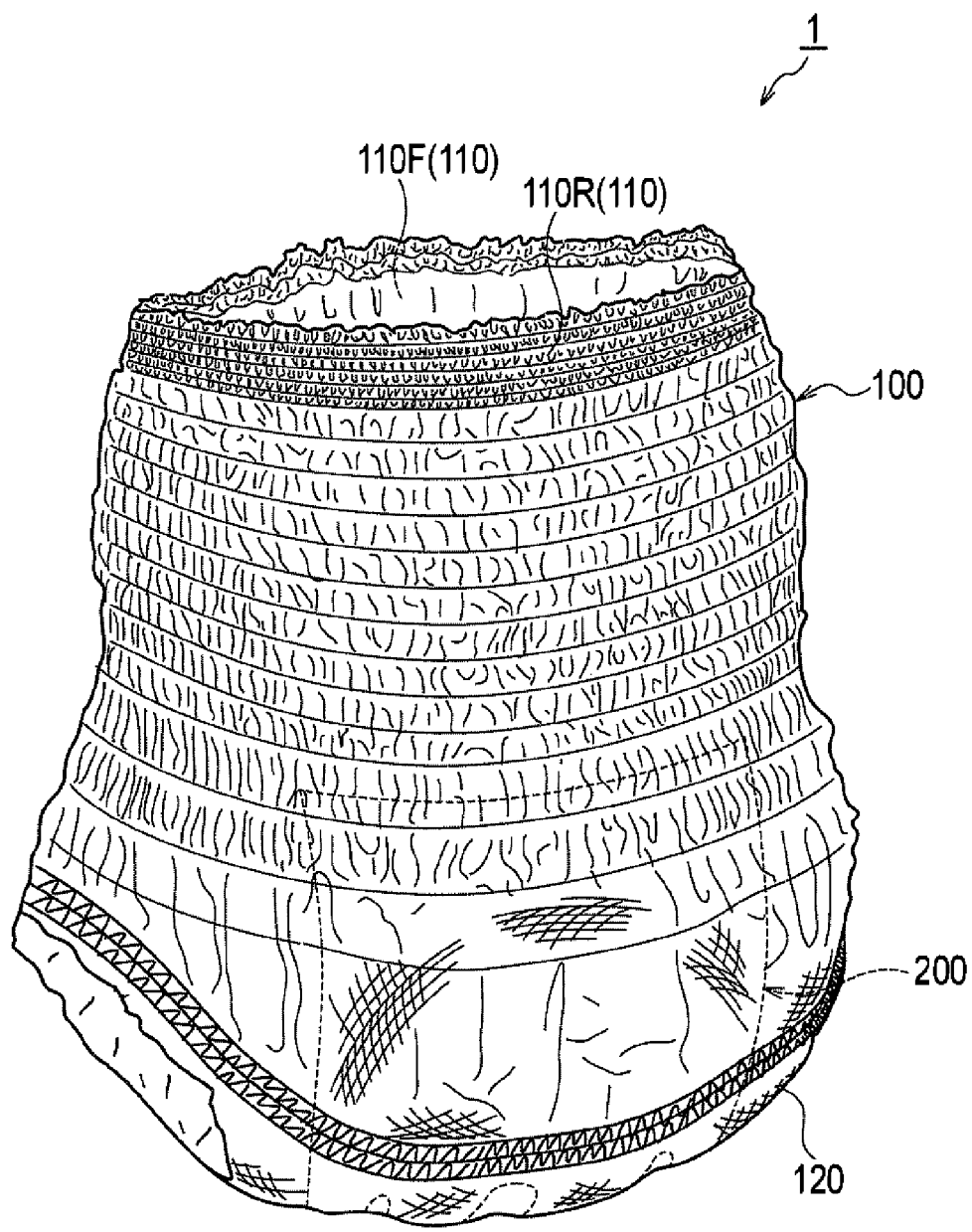
FIG. 1 is a perspective view showing a wearing article 1 according to a first embodiment.

Hereinafter, the wearing article according to the embodiments of the present invention is explained with reference to drawings. Note that in the description of the drawings below, the same or similar symbols have been used in the same or similar sections.

However, it should be noted that the diagrams are schematic and ratios of the respective dimensions do not determine the actual ones. Therefore, the specific dimensions, etc., should be determined in consideration of the following explanations. Moreover, it is needless to say that relations and ratios among the respective dimensions may differ among the diagrams.

Overview of Embodiments

Firstly, the wearing article according to an embodiment of the present invention includes a chassis having a waistline region and a crotch region, and an absorber main body with an absorber provided in at least the crotch region. The wearing article includes a first elastic member that is arranged such that it overlaps the absorber in the crotch region and extends along the longitudinal direction of the wearing article at an approximate center of the widthwise direction of the wearing article, and a second elastic member that curves within the crotch region from both ends of the waistline region in the widthwise direction of the wearing article and configures at least a part of the elastic stress line that crosses the absorber along the widthwise direction of the wearing article. In the elastic stress line, the elastic stress of the portion crossing the absorber is smaller than the elastic stress of the first elastic member.

Preferably, the first elastic member and the elastic stress line extend in directions which are approximately perpendicular to one another. The second elastic member is able to form at least part of the elastic stress line as follows. In some embodiments, the second elastic member follows all of the elastic stress line and therefore crosses the absorber along the widthwise direction of the wearing article. Thus, the second elastic member forms all of the elastic stress line. In some embodiments however, the second elastic member is discontinuous in a portion crossing the absorber; here the second elastic member does not have a portion crossing the absorber, or the portion of the second elastic member crossing the absorber is intermittent. When the second elastic member does not cross the absorber, the elastic stress line is nevertheless present. Here, the elastic stress line is formed by the effect of portions of the second elastic member at either side of the absorber. Embodiments are also envisaged wherein portions of the second elastic member are present at the side portions of the absorber but do not cross the whole width of the absorber either completely or intermittently.

The first and second elastic members may be the same or different. In one embodiment they each comprise a plurality of thread-shaped elastic members which extend in parallel but in different directions to one another. However, the invention is not to be limited to the presence of thread-shaped elastic members. The first and second elastic members could also be provided by a strip-shaped elastic sheet, for example.

Preferably, the first elastic member comprises between one and four thread-shaped elastic members and the second elastic member comprises between three and eight thread-shaped elastic members. To ensure the elastic stress of the portion crossing the absorber is smaller than the elastic stress of the first elastic member, the first elastic member may comprise fewer thread-shaped elastic members than the second elastic member.

The first elastic member is preferably dimensioned to be smaller than the absorber such that it is surrounded on all sides by the absorber. It is located at an approximate centre of a widthwise direction of the wearing article. The total width of the first elastic member is preferably a tenth to a third of the width of the absorber main body and is more preferably an eighth to a quarter of the width of the absorber main body.

The length of the first elastic member in the first embodiment is preferably a sixth to a third of the length of the absorber main body. Preferably, the first elastic member overlaps the centre of a lengthwise direction of the absorber main body. In some embodiments the first elastic member extends from an approximate centre of a lengthwise direction of the absorber main body towards either the front or rear of the absorber main body.

In general terms (and thus not limited to the exemplified embodiments), the first elastic member is arranged such that it overlaps the absorber in the crotch region and extends along the longitudinal direction of the wearing article at an approximate center of the widthwise direction of the wearing article. As a result, the contact between the excretion region of a wearer and the absorber is improved by the first elastic member. Therefore, even in cases where the urine flow is slow, the leakage of the urine outside the wearing article can be prevented. Further, in relation to the elastic stress line, the elastic stress of the portion crossing the absorber is smaller than the elastic stress of the first elastic member. As a result, in the portion crossing the absorber, a urine collector with relatively small elastic stress is formed. Therefore, even in cases where a large amount of urine is discharged, the leakage of the urine outside the wearing article can be prevented. Note that the urine collector is a space provided for temporary storage of the urine. With the help of the urine collector, time is provided to secure proper absorption of the urine by the absorber.

Secondly, the wearing article according to an embodiment of the present invention includes a chassis having a waistline region and a crotch region, and an absorber main body with an absorber provided in at least the crotch region of the chassis. The wearing article includes a first elastic member arranged such that it overlaps the absorber in the crotch region and extends along the longitudinal direction of the wearing article at an approximate center of the widthwise direction of the wearing article. The first elastic member includes a portion arranged to be directly under the crotch of a wearer that is provided at an approximate center portion of the wearing article in the longitudinal direction of the wearing article, and an extending portion that continues in succession to the portion arranged to be directly under the crotch in the longitudinal direction of the wearing article. The elastic stress of the extending portion is smaller than the elastic stress of the portion arranged to be directly under the crotch.

This second embodiment of the invention may be independent of or dependent on the first embodiment of the invention. The two portions of the first elastic member may be the same or different. In one embodiment they each comprise a plurality of thread-shaped elastic members which extend in parallel. However, the invention is not to be limited to the presence of thread-shaped elastic members. The first elastic member could also be provided by a strip-shaped elastic sheet, for example.

Preferably, the portion of the first elastic member arranged to be directly under the crotch of a wearer comprises between one and four thread-shaped elastic members and the extending portion of the first elastic member comprises between three and eight thread-shaped elastic members. To ensure the elastic stress of the extending portion is smaller than the elastic stress of the portion arranged to be directly under the crotch, the extending portion may comprise fewer thread-shaped elastic members than the portion arranged to be directly under the crotch.

In this second embodiment where the first elastic member has an extending portion, the widths given above for the first elastic member relative to the width of the absorber main body apply. However the length of the first elastic member, which comprises a portion arranged to be directly under the crotch of a wearer in use and an extending portion, is preferably approximately a third to a half of the length of the absorber main body. Preferably the first elastic member overlaps the approximate centre of a lengthwise direction of the main absorbent body.

In general terms (and thus not limited to the exemplified embodiments), the portion arranged to be directly under the crotch in the first elastic member is provided at an approximately center portion of the wearing article in the longitudinal direction of the wearing article. As a result, the contact between the excretion region of a wearer and the absorber is improved by the portion arranged to be directly under the crotch in the first elastic member. Therefore, even in cases where the urine flow is slow, the leakage of the urine outside the wearing article can be prevented. Further, in the first elastic member, the elastic stress of the extending portion is smaller than the elastic stress of the portion arranged to be directly under the crotch. That is, in the extending portion that continues in succession to the portion arranged to be directly under the crotch, a urine collector with relatively small elastic stress is formed. Therefore, even in cases where the amount of urine is large, the leakage of the urine outside the wearing article can be prevented. Note that the urine collector is a space provided for temporary storage of the urine. With the help of the urine collector, time is provided to secure proper absorption of the urine by the absorber.

First Embodiment (Configuration of Wearing Article)

Figure 2:
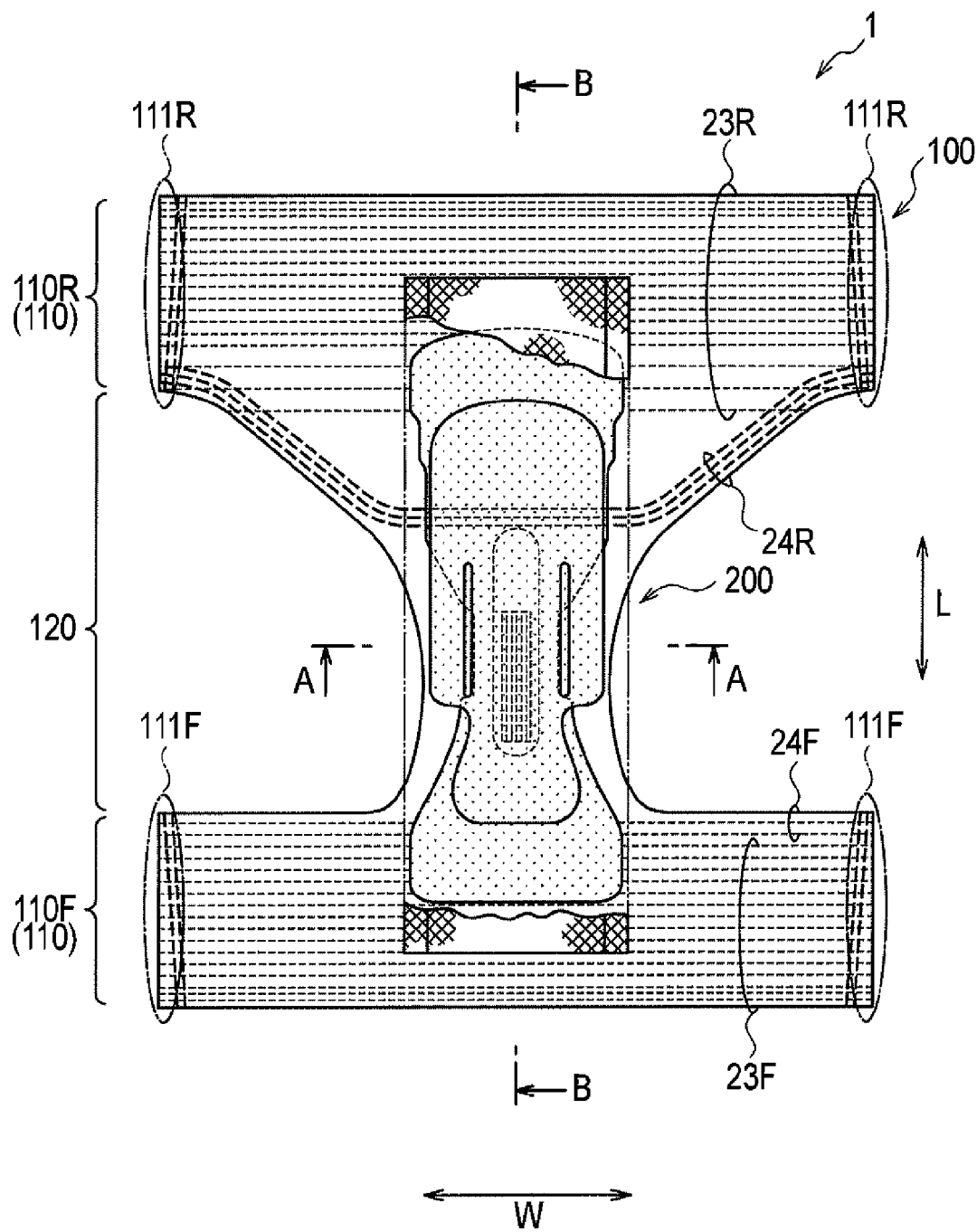
FIG. 2 is an exploded view showing the wearing article 1 according to the first embodiment.

Hereinafter, the configuration of the wearing article according to the first embodiment is schematically explained with reference to drawings. FIG. 1 is a perspective view showing a wearing article 1 according to the first embodiment. FIG. 2 is an exploded view showing the wearing article 1 according to the first embodiment.

In the first embodiment, a pants-type diaper is illustrated as an example of the wearing article 1. The wearing article 1 is, for example, an incontinence diaper. The wearing article 1 is, for example, a diaper used by the wearer for discharging urine with slow speed and for discharging a large amount of urine. In other words, the wearing article 1 is a diaper for wearers with an advanced degree of incontinence.

As shown in FIG. 1 and FIG. 2, the wearing article 1 has a chassis 100 and an absorber main body 200.

The chassis 100 forms the framework of the wearing article 1. The chassis 100 includes the waistline region 110 and the crotch region 120. The waistline region 110 includes the front waistline region 110F and the back waistline region 110R. The front waistline region 110F is in contact with the stomach of the wearer. The back waistline region 110R is the region that is in contact with the back of the wearer.

Note that in the widthwise direction W of the wearing article 1, a pair of side ends 111F of the front waistline region 110F and a pair of side ends 111R of the back waistline region 110R are joined. As a result, a pant-type wearing article 1 is formed.

The crotch region 120 is the region intermediate the front waistline region 110F and the back waistline region 110R.

Note that in the first embodiment, once fully assembled, the waistline region 110 is a strip-shaped region that extends along the widthwise direction W from the joined portion of the front waistline region 110F and the back waistline region 110R. Thus, the crotch region 120 includes the region where the size of the chassis 100 (width of the chassis 100) narrows down in the widthwise direction W facing an approximate center of the chassis 100 in the longitudinal direction L of the wearing article 1.

The absorber main body 200 includes an absorber that absorbs the urine of the wearer. The absorber main body 200 is provided on the skin surface side of the chassis 100. It is preferably adhered to the chassis along the whole length of the absorber main body.

(Detailed Configuration of Wearing Article)

Figure 3:
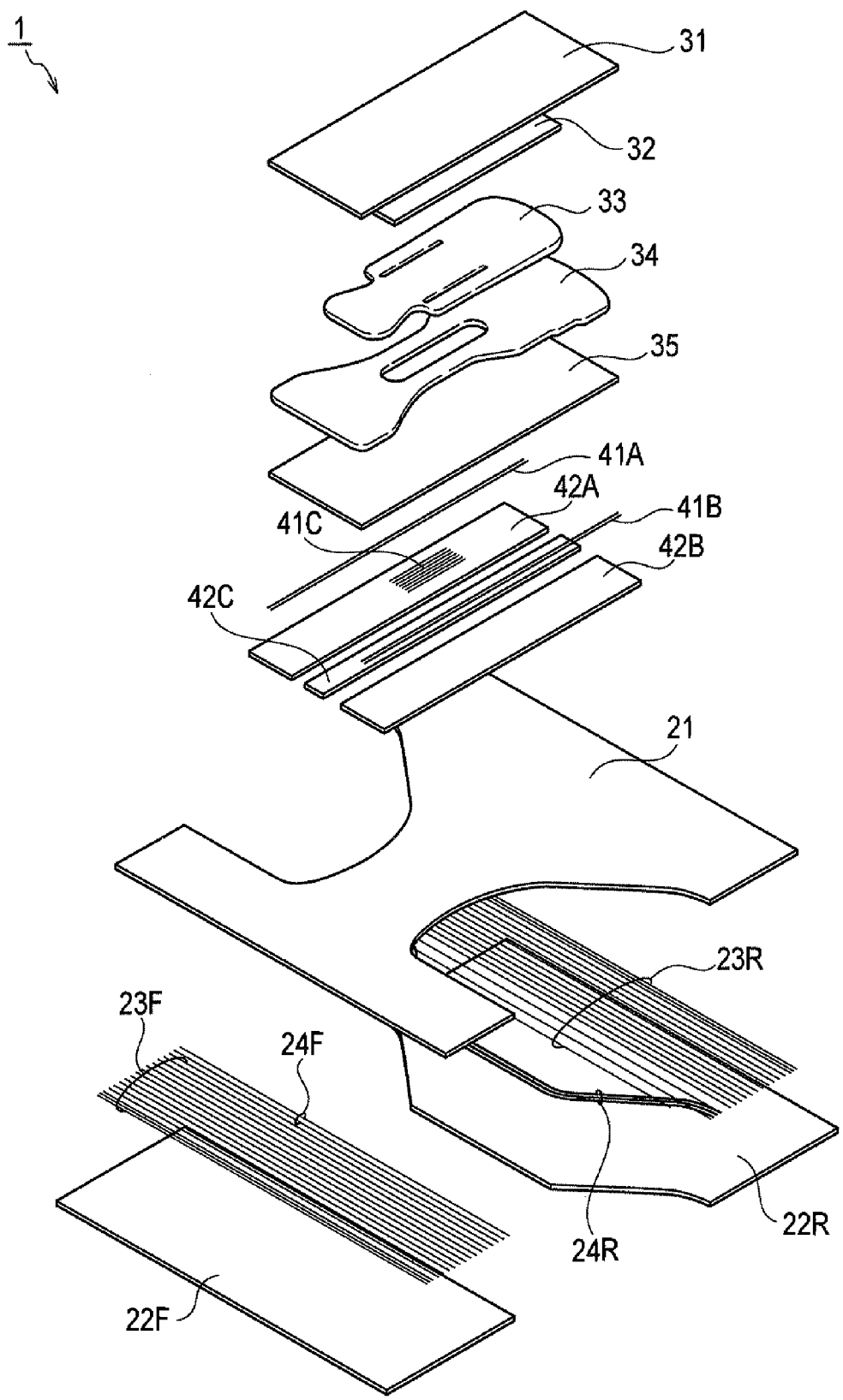
FIG. 3 is an exploded perspective view showing the wearing article 1 according to the first embodiment.
Figure 4:
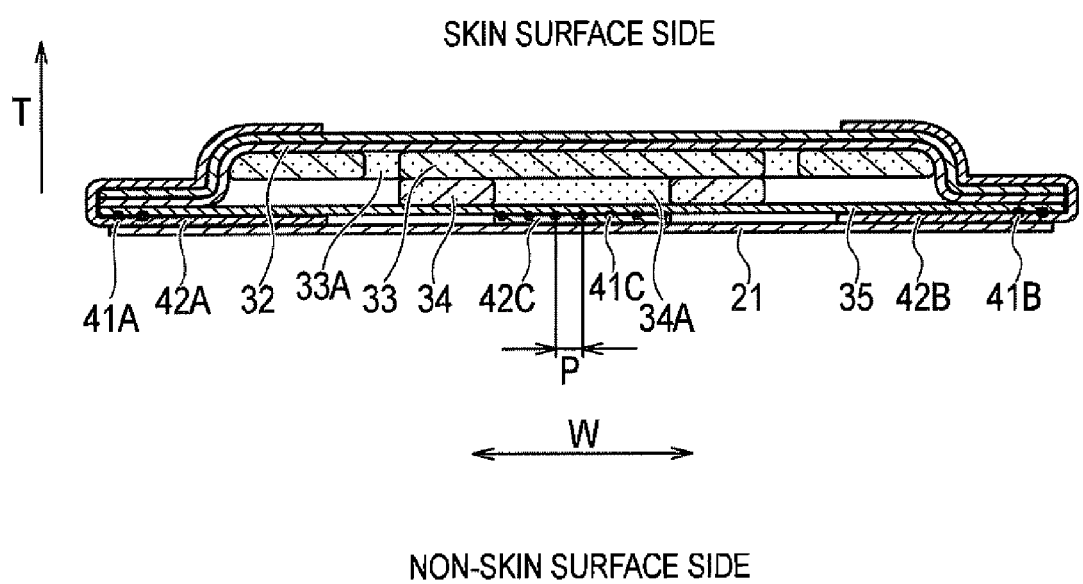
FIG. 4 is a cross-section diagram (A-A cross section shown in FIG. 2) showing the wearing article 1 according to the first embodiment.
Figure 5:
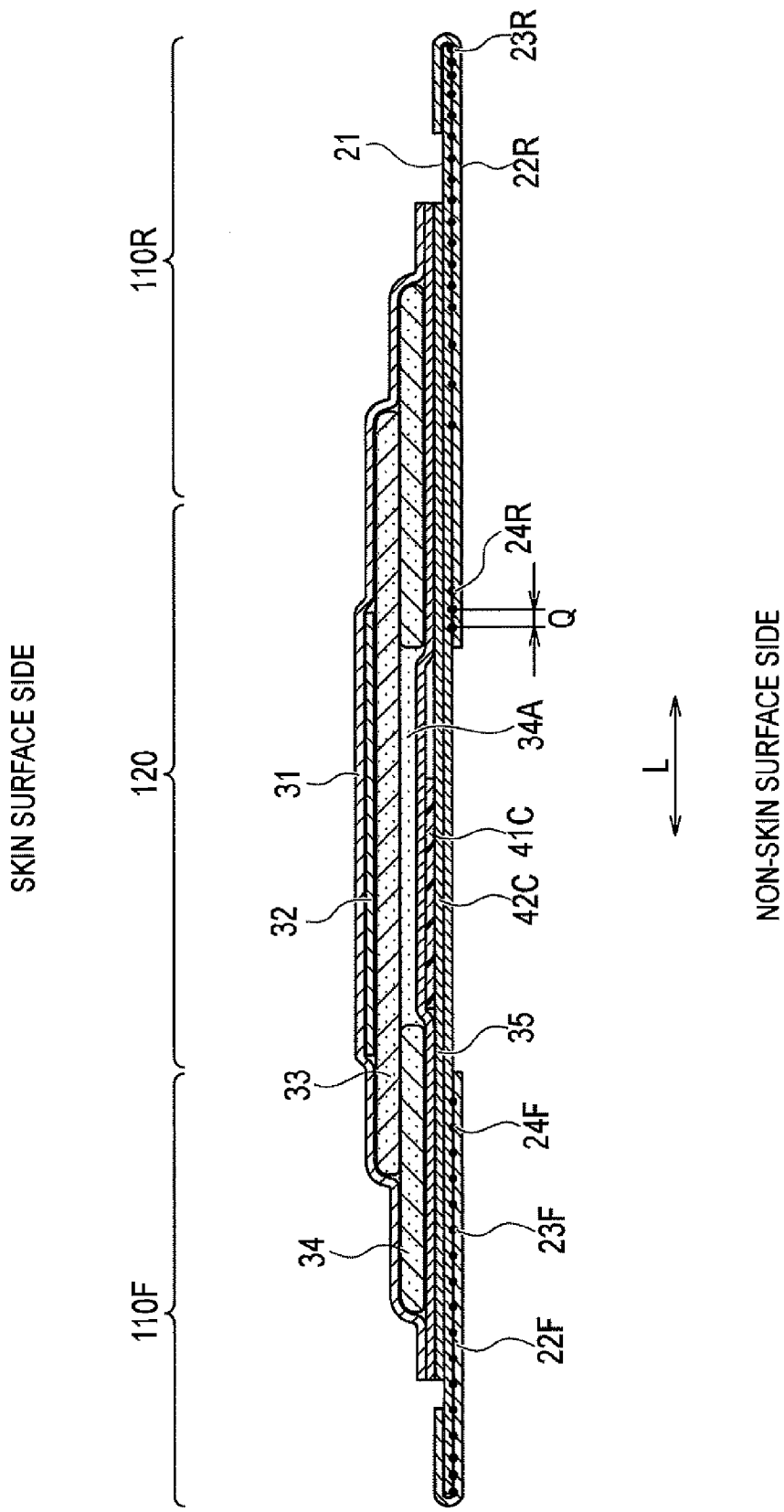
FIG. 5 is a cross-section diagram (B-B cross section shown in FIG. 2) showing the wearing article 1 according to the first embodiment.

Hereinafter, the detailed configuration of the wearing article according to the first embodiment is explained with reference to drawings. FIG. 3 is an exploded perspective view showing the wearing article 1 according to the first embodiment. FIG. 4 is a cross-section diagram (A-A cross section shown in FIG. 2) showing the wearing article 1 according to the first embodiment. FIG. 5 is a cross-section diagram (B-B cross section shown in FIG. 2) showing the cross section of the wearing article 1 according to the first embodiment.

As shown in FIG. 3, the wearing article 1 includes an exterior topsheet 21, a front exterior backsheet 22F, a back exterior backsheet 22R, a front waist elastic member 23F, a back waist elastic member 23R, a front leg elastic member 24F, and a back leg elastic member 24R. A different arrangement of layers and components may be used in other embodiments.

The exterior topsheet 21 is formed from the front waistline region 110F up to the back waistline region 110R via the crotch region 120. The width of the exterior topsheet 21 (size of the widthwise direction W) in the front waistline region 110F and the back waistline region 110R is larger than the size of the width of the exterior topsheet 21 (size of the widthwise direction W) in the crotch region 120. The exterior topsheet 21 may be formed by an air-through nonwoven fabric, a spun bond nonwoven fabric, an SMS nonwoven fabric, or a water-resistive film.

The front exterior backsheet 22F is provided towards the non-skin surface side from the exterior topsheet 21 in the front waistline region 110F. One end of the front exterior backsheet 22F in the longitudinal direction L is folded back on the skin surface side. The folded-back portion of the front exterior backsheet 22F wraps one end of the exterior topsheet 21 in the longitudinal direction L (for example, see FIG. 5).

The back exterior backsheet 22R is provided towards the non-skin surface side from the exterior topsheet 21 in the back waistline region 110R. One end of the back exterior backsheet 22R in the longitudinal direction L is folded back on the skin surface side. The folded back portion of the back exterior backsheet 22R wraps one end of the exterior topsheet 21 in the longitudinal direction L (for example, see FIG. 5).

The front exterior backsheet 22F and the back exterior backsheet 22R may be formed by an air-through nonwoven fabric, a spun bond nonwoven fabric, an SMS nonwoven fabric, or a water-resistive film.

The front waist elastic member 23F is provided between the exterior topsheet 21 and the front exterior backsheet 22F in the front waistline region 110F. For example, the front waist elastic member 23F includes a plurality of thread-shaped elastic bodies (such as rubber having elasticity). The front waist elastic member 23F is arranged along the widthwise direction W from both ends 111F of the front waistline region 110F in the widthwise direction W. In this example, the front waist elastic member 23F is joined between the exterior topsheet 21 and the front exterior backsheet 22F in an extended state along the widthwise direction W (for example, see FIG. 2 and FIG. 5), preferably using an adhesive (for example, a hot-melt adhesive).

The back waist elastic member 23R is provided between the exterior topsheet 21 and the back exterior backsheet 22R in the back waistline region 110R. For example, the back waist elastic member 23R includes a plurality of thread-shaped elastic bodies (such as rubber having elasticity). The back waist elastic member 23R is arranged along the widthwise direction W from both ends 111F of the back waistline region 110R in the widthwise direction W. In this example, the back waist elastic member 23R is joined between the exterior topsheet 21 and the back exterior backsheet 22R in an extended state along the widthwise direction W (for example, see FIG. 2 and FIG. 5), preferably using an adhesive (for example, a hot-melt adhesive).

The front leg elastic member 24F is provided between the exterior topsheet 21 and the front exterior backsheet 22F in the front waistline region 110F. For example, the front leg elastic member 24F includes a plurality of thread-shaped elastic bodies (such as rubber having elasticity).

In the first embodiment, the front leg elastic member 24F is arranged along the widthwise direction W in the front waistline region 110F. That is, the front leg elastic member 24F is arranged in an approximate straight line without curving within the crotch region 120 from both ends 111F of the front waistline region 110F in the widthwise direction W, although other arrangements may be used In this example, the front leg elastic member 24F is joined between the exterior topsheet 21 and the front exterior backsheet 22F in an extended state along the widthwise direction W (for example, see FIG. 2 and FIG. 5), preferably using an adhesive (for example, a hot-melt adhesive).

The back leg elastic member 24R is provided between the exterior topsheet 21 and the back exterior backsheet 22R in the back waistline region 110R, although alternative arrangements may be used. By way of example, the back leg elastic member 24R includes a plurality of thread-shaped elastic bodies (such as rubber having elasticity).

Here, the back leg elastic member 24R curves within the crotch region 120 from both ends of the back waistline region 110R in the widthwise direction W, and forms at least a part of the elastic stress line crossing the absorber (the first absorber layer 33 and the second absorber layer 34) provided in the absorber main body 200 in the widthwise direction W. However, as shown in FIG. 2, the back leg elastic member 24R may also be arranged such that it curves within the crotch region 120 from both ends of the back waistline region 110R in the widthwise direction W, and crosses the absorber (the first absorber layer 33 and the second absorber layer 34) provided in the absorber main body 200 in the widthwise direction W. That is, the back leg elastic member 24R may form the entire elastic stress line.

In this example, the back leg elastic member 24R is joined between the exterior topsheet 21 and the back exterior backsheet 22R in an extended state along the elastic stress line (for example, see FIG. 5), preferably using an adhesive (for example, a hot-melt adhesive).

Returning to FIG. 3, the wearing article 1 includes a topsheet 31, an absorber topsheet 32, the first absorber layer 33, the second absorber layer 34, and an absorber backsheet 35, although the invention is not to be limited to this arrangement.

The topsheet 31 is a sheet that forms the skin contact surface that can be in direct contact with the wearer's skin. The topsheet 31 is formed by a liquid-permeable sheet, such as a hydrophilic nonwoven fabric and woven cloth, an apertured plastic film, or an apertured hydrophobic nonwoven fabric.

The absorber topsheet 32 is provided on the skin surface side of the absorber (the first absorber layer 33 and the second absorber layer 34). That is, the absorber topsheet 32 is provided between the topsheet 31 and the absorber (the first absorber layer 33 and the second absorber layer 34) (for example, see FIG. 4). The absorber topsheet 32 is formed by a liquid-permeable sheet, such as a hydrophilic nonwoven fabric and woven cloth, an apertured plastic film, an apertured hydrophobic nonwoven fabric, or a tissue. Note that in the longitudinal direction L, the absorber topsheet 32 is shorter than the topsheet 31.

The first absorber layer 33 forms a part of the absorber and is provided on the skin surface side of the wearer. The first absorber layer 33 includes a slit 33A extending along the longitudinal direction L, although this slit is not essential to the present invention.

The second absorber layer 34 forms a part of the absorber and is provided on the non-skin surface side of the wearer. The second absorber layer 34 includes an aperture 34A at an approximate center of the widthwise direction W (for example, see FIG. 4), although this aperture is not essential to the invention. The aperture 34A has a longitudinally elongated shape extending along the longitudinal direction L. In one example, the size (length) of the aperture 34A in the longitudinal direction L is approximately 200 mm, and the size (width) of the aperture 34A in the widthwise direction W is approximately 40 mm.

The first absorber layer 33 and the second absorber layer 34 are preferably formed of cotton-like pulp and highly polymerized water absorbent polymer (SAP). By way of example, the first absorber layer 33 is formed by mixing together 200 $g/m^2$ of pulp and 90 $g/m^2$ of SAP, and its thickness in the thickness direction T is approximately 2.0 mm. By way of example, the second absorber layer 34 is formed by mixing together 300 $g/m^2$ of pulp and 150 $g/m^2$ of SAP, and its thickness in the thickness direction T is approximately 3.0 mm. Other examples are envisaged using different mixtures and having other thicknesses.

The absorber backsheet 35 is provided on the non-skin surface side of the absorber (the first absorber layer 33 and the second absorber layer 34) (for example, see FIG. 4). The absorber backsheet 35 is formed by a sheet such as a liquid-impermeable film (for example, polyethylene).

Returning to FIG. 3, the wearing article 1 includes a leakage-preventing elastic member 41A, a leakage-preventing elastic member 41B, a central elastic member 41C, a leakage-preventing elastic member sheet 42A, a leakage-preventing elastic member sheet 42B, and a central elastic member covering sheet 42C, although the invention is not to be limited to this arrangement.

In this example, the leakage-preventing elastic member 41A is provided at one outer side of the absorber (the first absorber layer 33 and the second absorber layer 34) in the widthwise direction W in the crotch region 120. The leakage-preventing elastic member 41A is arranged along the longitudinal direction L. For example, the leakage-preventing elastic member 41A includes a plurality of thread-shaped elastic bodies (such as rubber having elasticity). In one example, the leakage-preventing elastic member 41A is joined between the leakage-preventing elastic member sheet 42A and the absorber backsheet 35 in an extended state along the longitudinal direction L (for example, see FIG. 4), preferably using an adhesive (for example, a hot-melt adhesive).

The leakage-preventing elastic member 41B is provided, in this example, at the other outer side of the absorber (the first absorber layer 33 and the second absorber layer 34) in the widthwise direction W in the crotch region 120. The leakage-preventing elastic member 41B is arranged along the longitudinal direction L. For example, the leakage-preventing elastic member 41B includes a plurality of thread-shaped elastic bodies (such as rubber having elasticity). In one example, the leakage-preventing elastic member 41B is joined between the leakage-preventing elastic member sheet 42B and the absorber backsheet 35 in an extended state along the longitudinal direction L (for example, see FIG. 4), preferably using an adhesive (for example, a hot-melt adhesive).

The central elastic member 41C overlaps the absorber (the first absorber layer 33 and the second absorber layer 34) in the crotch region 120. Further, the central elastic member 41C is arranged such that it extends along the longitudinal direction L at an approximate center of the widthwise direction W. Note that the central elastic member 41C is provided on the non-skin surface side (i.e. the non-skin-facing surface or side) of the absorber (the first absorber layer 33 and the second absorber layer 34). Also note that the purpose and meaning of the "non-skin surface side" in this context is to exclude the "skin surface side" (i.e. the skin-facing surface or side). For example, in the first embodiment, if the second absorber layer 34 includes the aperture 34A, the central elastic member 41C may be provided within the aperture 34A. Alternatively, with the absorber being configured by the first absorber layer 33 and the second absorber layer 34, the central elastic member 41C may be arranged between the first absorber layer 33 and the second absorber layer 34. In both cases, the central elastic member 41C is not on the skin-facing surface or side of the absorber. Instead, if overlaps the non-skin-facing surface or side of the absorber.

By way of example, the central elastic member 41C includes a plurality of thread-shaped elastic bodies (such as rubber having elasticity). In one example, the central elastic member 41C is joined between the central elastic member covering sheet 42C and the absorber backsheet 35 in an extended state along the longitudinal direction L (for example, see FIG. 4), preferably using an adhesive (for example, a hot-melt adhesive)

As an example, should the central elastic member 41C be provided on the non-skin surface side of the absorber, the central portion of the absorber in the longitudinal direction L would curve on the skin surface side due to the elastic stress of the central elastic member 41C, and the contact between the excretion region and the absorber would decline. In contrast, in the first embodiment, because the central elastic member 41C is provided on the non-skin surface side of the absorber, such a decline in the contact is inhibited.

The leakage-preventing elastic member sheet 42A is preferably folded back at one end of the absorber (the first absorber layer 33 and the second absorber layer 34) in the widthwise direction W. The folded-back portion of the leakage-preventing elastic member sheet 42A wraps one end of the topsheet 31, the absorber topsheet 32, and the absorber backsheet 35 in the widthwise direction W (for example, see FIG. 4).

The leakage-preventing elastic member sheet 42B is preferably folded back at the other end of the absorber (the first absorber layer 33 and the second absorber layer 34) in the widthwise direction W. The folded-back portion of the leakage-preventing elastic member sheet 42B wraps the other end of the topsheet 31, the absorber topsheet 32, and the absorber backsheet 35 in the widthwise direction W (for example, see FIG. 4).

The leakage-preventing elastic member sheet 42A and the leakage-preventing elastic member sheet 42B are formed by a sheet such as a liquid-impermeable nonwoven fabric. The leakage-preventing elastic member sheet 42A, the leakage-preventing elastic member sheet 42B, the leakage-preventing elastic member 41A and the leakage-preventing elastic member 41B configure the leakage-preventing wall that prevents side leakage of urine. Alternative components or arrangements may be used to achieve the same effect.

In this embodiment, the central elastic member covering sheet 42C is provided between the exterior topsheet 21 and the absorber backsheet 35, although other arrangements may be used. As described above, the central elastic member 41C is arranged between the central elastic member covering sheet 42C and the absorber backsheet 35, although other arrangements may be used.

Here, in the first embodiment, the central elastic member 41C comprises a plurality of thread-shaped elastic members extending approximately in parallel in the longitudinal direction. The back leg elastic member 24R also comprises a plurality of thread-shaped elastic members extending approximately in parallel and extending in a different direction to the thread-shaped elastic members of the central elastic member. Where the back leg elastic members cross the absorber, its thread-shaped elastic members extend in the widthwise direction of the wearing article. Preferably, the distance or interval P between a pair of adjacent thread-shaped elastic members configuring the central elastic member 41C (see FIG. 4) is smaller than the distance or interval Q between a pair of adjacent thread-shaped elastic members configuring the portion that crosses the absorber in the back leg elastic member 24R (see FIG. 5). Further, the elastic stress of one thread-shaped elastic member forming the back leg elastic member 24R is desired to be more than the elastic stress of one thread-shaped elastic member forming the central elastic member 41C. In such a case, because the interval P is smaller than the interval Q, the contact of the absorber to the excretion region is high due to the central elastic member 41C. On the other hand, because the interval Q is larger than the interval P, the fitting of the wearing article 1 against the skin around the leg of the wearer is loose and the wearing article 1 may be partially not pressed against the skin around the leg of the wearer, meaning that the tightening feeling caused by the elastic members at the time of wearing can be softened.

Further, in the first embodiment, the back leg elastic member 24R is arranged towards the non-skin surface side from the central elastic member 41C (see FIG. 5). That is, the back leg elastic member 24R is provided at a position farther away from the absorber than the central elastic member 41C and is positioned closer to the non-skin surface side of the wearing article than the central elastic member is. Thus, in the back leg elastic member 24R, it becomes difficult to constrict the width of the absorber (the size of the absorber in the widthwise direction W) in the portion crossing the absorber and thus the decline in the contact between the excretion region of a wearer and the absorber is inhibited. On the other hand, the central elastic member 41C is provided at a position closer to the absorber than the back leg elastic member 24R is. Therefore, the absorber is easily deformed to contact the excretion region.

Note that in the first embodiment, the absorber main body 200 is configured by the topsheet 31, the absorber topsheet 32, the first absorber layer 33, the second absorber layer 34, and the absorber backsheet 35. Alternative arrangements may be used to configure the absorber main body. Also, in addition to this arrangement, the absorber main body 200 may be configured by the leakage-preventing elastic member 41A, the leakage-preventing elastic member 41B, the central elastic member 41C, the leakage-preventing elastic member sheet 42A, the leakage-preventing elastic member sheet 42B, and the central elastic member covering sheet 42C, or an alternative arrangement of elastic members and sheets, in accordance with the teachings of the present invention (Relationship Among Elastic Stresses)

Hereinafter, the relationship among the elastic stresses according to the first embodiment is explained with reference to drawings. Pattern 1 to pattern 4 are explained below with reference to FIG. 6 to FIG. 9. Note that the entire wearing article 1 in the longitudinal direction L is shown in FIG. 6 to FIG. 9.

As shown in FIG. 6 to FIG. 9, the wearing article 1 has the following configuration as common configuration in pattern 1 to pattern 4. Specifically, the wearing article 1 includes the back waistline region 110R and the crotch region 120. The crotch region 120 includes a region 120M arranged to be directly under the crotch of a wearer and a middle region 120R.

The region 120M, arranged to be directly under the crotch, is the region that is in contact with the crotch (excretion region) of the wearer where the width between the two legs when the wearer closes both legs is the narrowest. The middle region 120R is the region intermediate the region 120M (arranged to be directly under the crotch) and the back waistline region 110R.

The above-mentioned central elastic member 41C is arranged such that it extends along the longitudinal direction L in the region 120M i.e. directly under the crotch. However, the central elastic member 41C does not reach the middle region 120R.

The above-mentioned elastic stress line 310 curves within the crotch region 120 from both ends of the back waistline region 110R in the widthwise direction W, and crosses the absorber (the first absorber layer 33 and the second absorber layer 34) provided in the absorber main body 200 in the widthwise direction W.

Here, in the elastic stress line 310, the elastic stress of the portion crossing the absorber is common in pattern 1 to pattern 4, and is smaller than the elastic stress of the central elastic member 41C. Thus, in the middle region 120R, a urine collector 320 with a relatively small elastic stress is formed in the portion that crosses the absorber, in the elastic stress line 310. Note that the urine collector 320 is a space provided for temporary storage of the urine. With the help of the urine collector, time is provided to secure proper absorption of the urine by the absorber.

Note that in the following explanations, the desirable values for stress ranges and stress ratios of the central elastic member 41C and the back leg elastic member 24R are as follows. The stress range of the central elastic member 41C is desirably 0.05 to 1.0 N/cm, the stress range of the back leg elastic member 24R (absorber crossing portion) is desirably 0 to 0.4 N/cm, and the stress range of the back leg elastic member 24R (non-absorber crossing portion) is desirably 0.2 to 3.0 N/cm. The stress ratio between the back leg elastic member 24R (absorber crossing portion) and the central elastic member 41C is desirably below 1.0, the stress ratio between the back leg elastic member 24R (absorber crossing portion) and the back leg elastic member 24R (non-absorber crossing portion) is desirably below 0.9, and the stress ratio between the central elastic member 41C and the back leg elastic member 24R (non-absorber crossing portion) is desirably below 0.9.

(Pattern 1)

Figure 6:
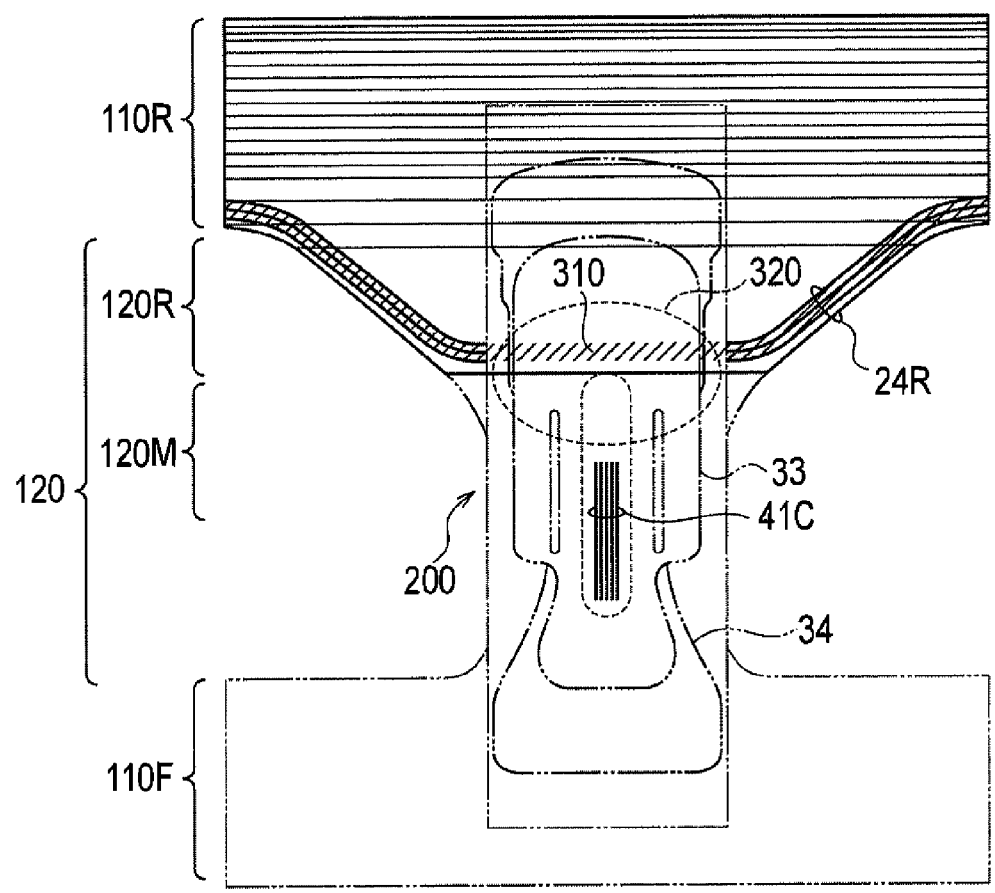
FIG. 6 is a diagram for explaining Pattern 1 according to the first embodiment.

Hereinafter, pattern 1 is explained with reference to FIG. 6. As shown in FIG. 6, the back leg elastic member 24R forms a part of the elastic stress line 310. The back leg elastic member 24R is discontinuous in the portion crossing the absorber on the elastic stress line 310. That is, the back leg elastic member 24R is not provided in the portion crossing the absorber on the elastic stress line 310. Therefore, in the elastic stress line 310, the elastic stress of the portion crossing the absorber is smaller than the elastic stress of the central elastic member 41C.

Note that in pattern 1, the elastic stress of the back leg elastic member 24R is desired to be more than the elastic stress of the central elastic member 41C.

(Pattern 2)

Figure 7:
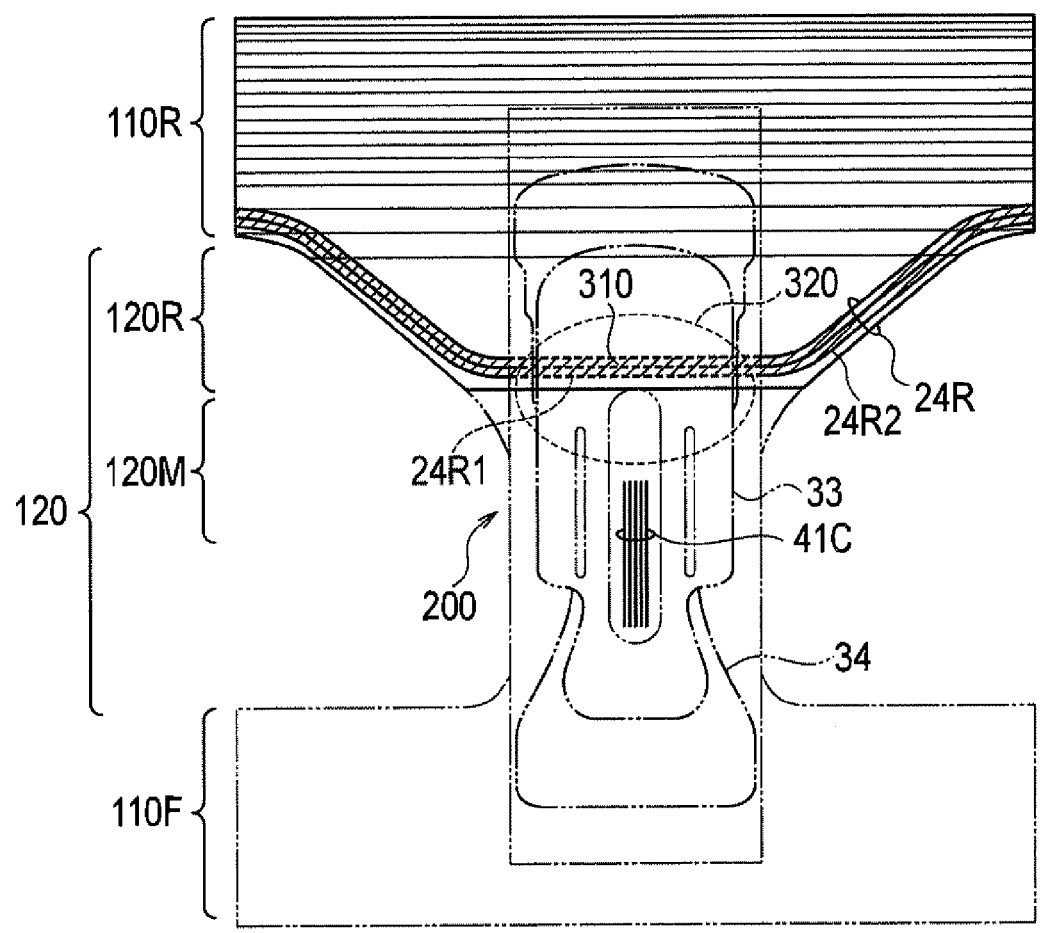
FIG. 7 is a diagram for explaining Pattern 2 according to the first embodiment.

Hereinafter, pattern 2 is explained with reference to FIG. 7. As shown in FIG. 7, the back leg elastic member 24R forms the entire elastic stress line 310.

The back leg elastic member 24R includes the crossing portion 24R1 and the non-crossing portion 24R2. The crossing portion 24R1 forms the portion crossing the absorber in the elastic stress line 310. The non-crossing portion 24R2 forms the portion other than the portion crossing the absorber in the elastic stress line 310.

In pattern 2, the crossing portion 24R1 is cut off intermittently. For example, in the crossing portion 24R1, an intermittent perforated tear-off line is made by a cutter. That is, the back leg elastic member 24R remains as a dotted line in the portion crossing the absorber on the elastic stress line 310. Thus, the elastic stress of the crossing portion 24R1 becomes smaller than the elastic stress of the central elastic member 41C.

Note that in pattern 2, the elastic stress of the non-crossing portion 24R2 is desired to be more than the elastic stress of the crossing portion 24R1, and also more than the elastic stress of the central elastic member 41C.

(Pattern 3)

Figure 8:
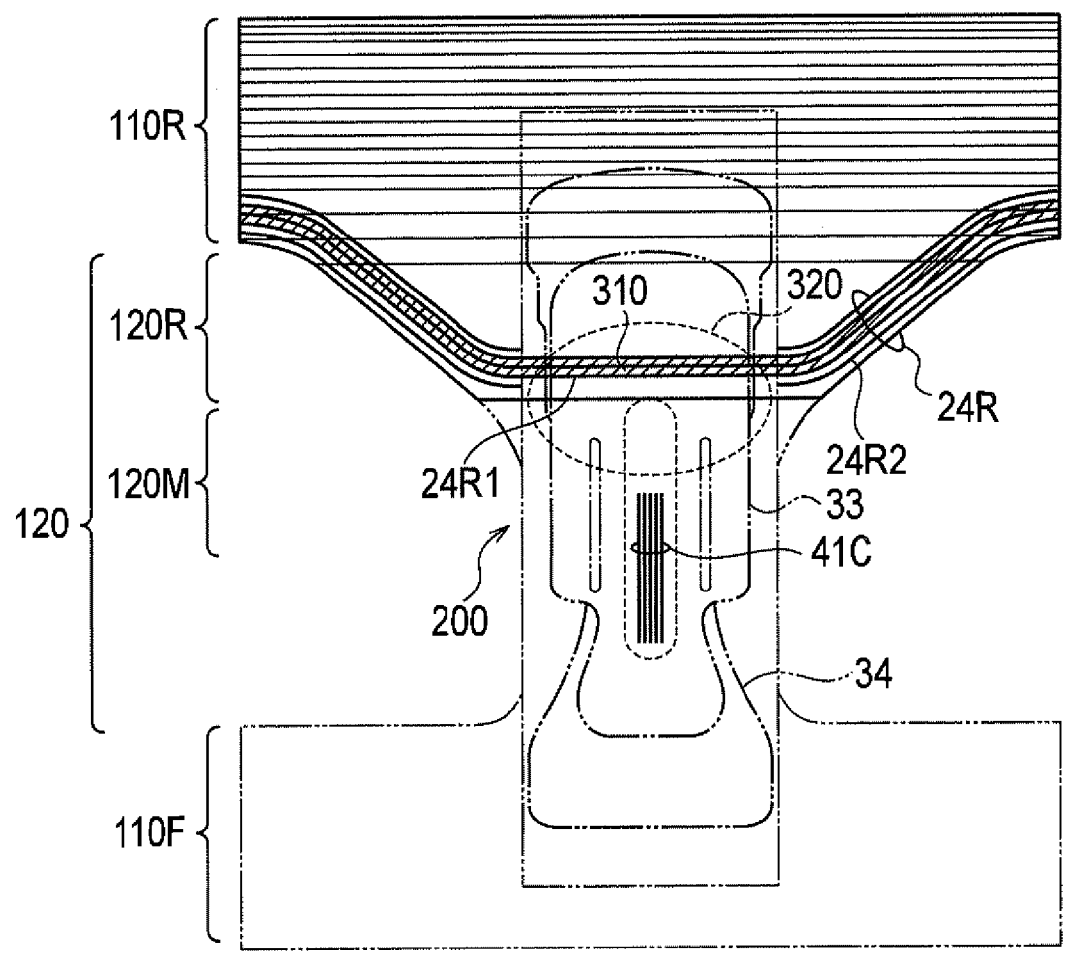
FIG. 8 is a diagram for explaining Pattern 3 according to the first embodiment.

Hereinafter, pattern 3 is explained with reference to FIG. 8. As shown in FIG. 8, the back leg elastic member 24R configures the entire elastic stress line 310.

The back leg elastic member 24R includes the crossing portion 24R1 and the non-crossing portion 24R2. The crossing portion 24R1 forms the portion crossing the absorber in the elastic stress line 310. The non-crossing portion 24R2 forms the portion other than the portion crossing the absorber in the elastic stress line 310.

In pattern 3, the back leg elastic member 24R is configured by a plurality of thread-shaped elastic members. The number of thread-shaped elastic members configuring the crossing portion 24R1 is smaller (for example, 3 elastic members) than the number of thread-shaped elastic members configuring the non-crossing portion 24R2 (for example, 5 elastic members). Thus, the elastic stress of the crossing portion 24R1 becomes smaller than the elastic stress of the central elastic member 41C.

Note that in pattern 3, the elastic stress of the non-crossing portion 24R2 is desired to be more than the elastic stress of the crossing portion 24R1, and also more than the elastic stress of the central elastic member 41C.

(Pattern 4)

Figure 9:
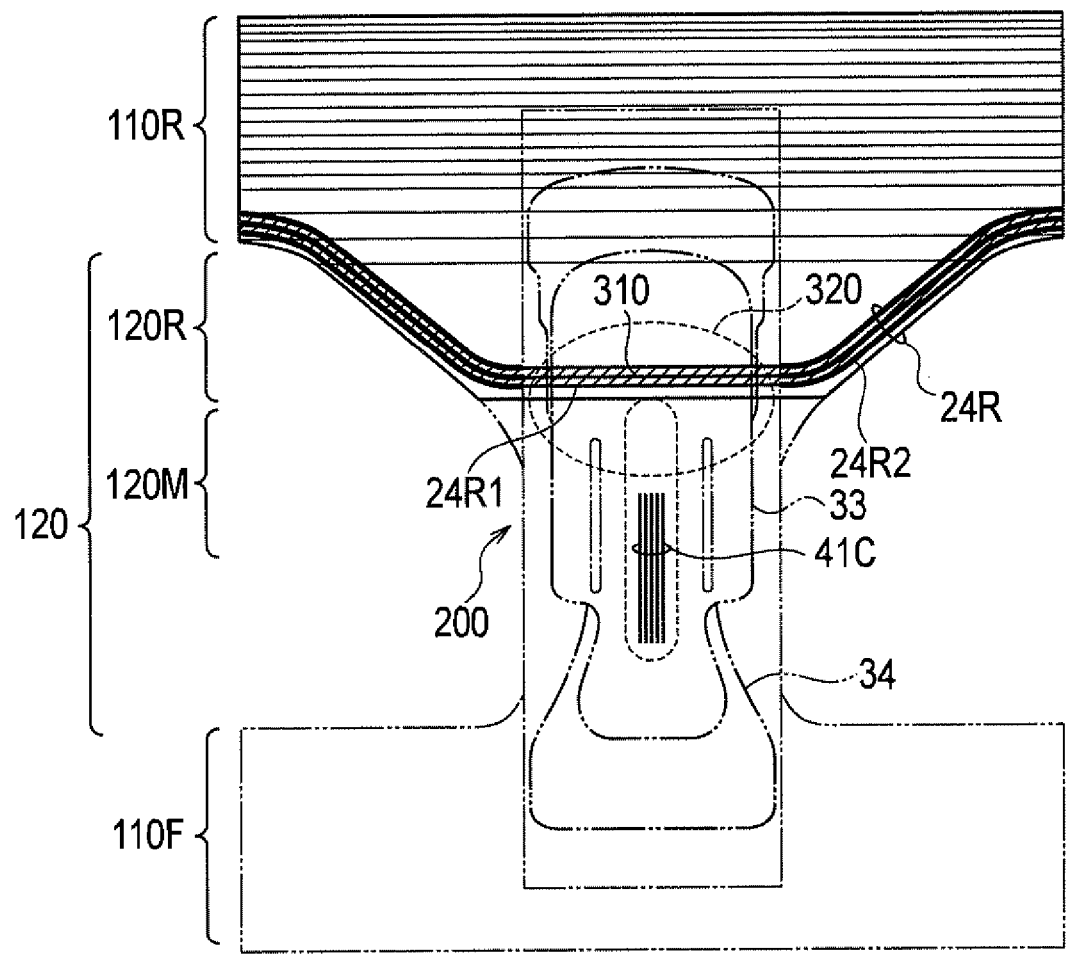
FIG. 9 is a diagram for explaining Pattern 4 according to the first embodiment.

Hereinafter, pattern 4 is explained with reference to FIG. 9. As shown in FIG. 9, the back leg elastic member 24R forms the entire elastic stress line 310.

The back leg elastic member 24R includes the crossing portion 24R1 and the non-crossing portion 24R2. The crossing portion 24R1 forms the portion crossing the absorber in the elastic stress line 310. The non-crossing portion 24R2 forms the portion other than the portion crossing the absorber in the elastic stress line 310.

In pattern 4, the elastic stress of the crossing portion 24R1 is smaller than the elastic stress of the non-crossing portion 24R2.

This may be achieved, for example, when the back leg elastic member 24R is arranged between the exterior topsheet 21 and the back exterior backsheet 22R; the elastic stress of the crossing portion 24R1 and of the non-crossing portion 24R2 can be changed by changing the degree of extension of the back leg elastic member 24R in these distinct portions. Further, or as an alternative, the crossing portion 24R1 and the non-crossing portion 24R2 may be configured by different types of materials.

Note that in pattern 4, the elastic stress of the non-crossing portion 24R2 is desired to be more than the elastic stress of the crossing portion 24R1, and also more than the elastic stress of the central elastic member 41C.

Generally-speaking, when the thread-shaped elastic members are identical elastic members, the elastic stress of the portion in which the thread-shaped elastic members are arranged is higher when a larger number of thread-shaped elastic members is used. When the thread-shaped elastic members are identical elastic members and the number of the thread-shaped elastic members is the same, the elastic stress of the portion in which the thread-shaped elastic members are arranged is higher when thicker thread-shaped elastic members are used.

Here, the extension rate of the crossing portion 24R1 is, for example, 50% to 300%. That is, the extension magnitude of the crossing portion 24R1 is, for example, 1.5 times to 4.0 times. The extension rate of the non-crossing portion 24R2 is, for example, below 80%. That is, the extension magnitude of the non-crossing portion 24R2 is, for example, below 1.8 times. The extension rate of the central elastic member 41C is, for example, 20% to 200%. That is, the extension magnitude of the crossing portion 24R1 is, for example, 1.2 times to 3 times.

Further, the elastic stress of the portion in which the elastic members being thread-shaped are arranged can be measured with the following procedure. Note that in the portion in which thread-shaped elastic members are arranged, for example, consideration must be given to the fact that the thread-shaped elastic members are sandwiched by a pair of fabric sheets, such as nonwoven fabric sheets. This measurement method is also applicable to elastic members which do not comprise a plurality of thread-shaped elastic members, for example strip-shaped elastic members.

(1) In the relaxed state (non-extended state), the portion in which the thread-shaped elastic members are arranged (portion to be measured) is cut. For example, the length of the portion to be measured is 150 mm in the direction in which the thread-shaped elastic members are extending (hereinafter referred to as the extension direction), and the width of the portion to be measured is 25 mm in the direction that is approximately orthogonal to the extension direction.

(2) The portion to be measured is extended along the extension direction until the portion to be measured becomes equivalent to the natural length. Next, in the extension direction, a pair of markers are added to the portion to be measured at a predetermined marking interval (natural length). For example, the predetermined marking interval of a pair of markers (natural length) is 100 mm.

(3) The portion to be measured is left in the relaxed state. For example, the portion to be measured is left for 24 hours under a constant temperature (20 to 23° C.) and constant humidity (60 to 65% RH). The reason for leaving the portion to be measured under a constant temperature and constant humidity is because it is necessary to maintain the portion under fixed conditions until the stress return stabilizes. Further, the following tensile test is performed under an environment wherein the above-mentioned constant temperature and constant humidity are the same so as not to influence the elasticity.

(4) In the tensile testing machine, both sides of the portion to be measured are chucked at the pair of markers in the extension direction and in the relaxed state. Next, the portion to be measured is extended in the tensile testing machine until the marker interval becomes equivalent to the predetermined marking interval (measurement). The predetermined marking interval (measurement) is narrower than the predetermined marking interval (natural length). For example, the predetermined marking interval (measurement) is 70% of the predetermined marking interval (natural length). Further, the extension speed of the portion to be measured is 100 mm/min. Note that the reason for having the predetermined marking interval (measurement) narrower than the predetermined marking interval (natural length) is to prevent tearing of the fabric, such as a nonwoven fabric, which sandwiches the thread-shaped elastic members. Further, for example, the Autograph Tensile Testing Machine (model name: AG-I) made by Shimadzu Corporation can be used as the tensile testing machine.

(5) The stress (elastic stress) working in the portion to be measured is measured in the extended state until the marker interval becomes equivalent to the predetermined marking interval (measurement). Note that the unit of the elastic stress is N, for example.

However, when comparing the elastic stress, it must be taken into consideration that the number of thread-shaped elastic members included in the portion to be measured may be different. For example, in the above-mentioned pattern 3, the number of thread-shaped elastic members included in the portion to be measured that is cut out from the crossing portion 24R1 is smaller than the number of thread-shaped elastic members included in the portion to be measured that is cut out from the non-crossing portion 24R2.

Specifically, gathers a stress of which is desired to be measured are cut out by a gather width (for example, gathers configured by four elastic members), and the whole stress of the cut-out gathers is measured. The measured whole stress is converted into a stress per 10 mm (1 cm) in accordance with the cut-out gather width, and the converted value is set to a stress of gathers. A comparison is made to the elastic stresses converted as described above.

For example, in a case where the gathers taken out by a width of 25 mm contain four elastic members, a distance between the outermost sides of these four elastic members (between the outward end in the width direction of the first elastic member and the outward end in the width direction of the fourth elastic member out of these four elastic members) is 15 mm, and a measured value is A, a stress value X1 per unit width is determined by X1=A×10/15 (N/cm). In a case where an interval between the elastic members (a distance between the outermost sides) is partially different in the portion to be measured, an approximate average value of intervals in the portion to be measured is determined and used for calculation.

Further, if the elastic members are sheet shaped instead of thread shaped, the width of the elastic members included in the acquisition width can be obtained (C mm), and then the result can be acquired by dividing the measurement value with this width. Here, if the measurement value is A', the stress value X2 for the unit width will become $X2=A'\div C\times 10$ (N/cm). When acquiring the measurement sample, consideration must be given such that the elastic members other than the target elastic members are not included.

According to the embodiment, the central elastic member 41C is arranged such that it overlaps the absorber in the crotch region 120 and extends along the longitudinal direction L at an approximate center of the widthwise direction W. As a result, the contact between the excretion region and the absorber is improved by the central elastic member 41C. Therefore, even in cases where the urine flow is slow, the leakage of the urine outside the wearing article 1 can be prevented. Further, in the elastic stress line, the elastic stress of the portion crossing the absorber (for example, the crossing portion 24R1) is smaller than the elastic stress of the central elastic member 41C. As a result, in the portion crossing the absorber (for example, the middle region 120R) a urine collector 320 with a relatively small elastic stress is formed. Therefore, even in cases where the amount of urine discharged is large, the leakage of the urine outside the wearing article 1 can be prevented.

According to the embodiment, the elastic stress of the back leg elastic member 24R (for example, the non-crossing portion 24R2) is more than the elastic stress of the central elastic member 41C. Therefore, even in cases where urine is collected in the urine collector 320, slipping down of the wearing article 1 as a result of the weight of the urine can be prevented due to the lifting effect of the back leg elastic member 24R (for example, the non-crossing portion 24R2).

According to the embodiment, because the interval P of the plurality of thread-shaped elastic members configuring the central elastic member 41C is smaller than the interval Q of the plurality of thread-shaped elastic members configuring the back leg elastic member 24R, the contact of the absorber to the excretion region is high due to the central elastic member 41C. On the other hand, because the interval Q is larger than the interval P, the fitting of the wearing article 1 against the skin around the leg of the wearer is loose and the wearing article 1 may partially not be pressed against the skin around the leg of the wearer, meaning that the tightening feeling caused by the elastic members at the time of wearing can be softened.

[First Modification]

Hereinafter, the first modification of the first embodiment is explained with reference to drawings. The explanation below is based primarily on the differences with respect to the first embodiment.

Specifically, in the first embodiment, the central elastic member 41C does not reach the middle region 120R. In contrast, in the first modification, the central elastic member 41C reaches the middle region 120R.

(Relationship Among Elastic Stresses)

Hereinafter, the relationship between the elastic stresses according to the first modification is explained with reference to drawings. Pattern 5 to pattern 7 are explained below with reference to FIG. 10 to FIG. 12. Note that the entire wearing article 1 in the longitudinal direction L is shown in FIG. 10 to FIG. 12.

Figure 10:
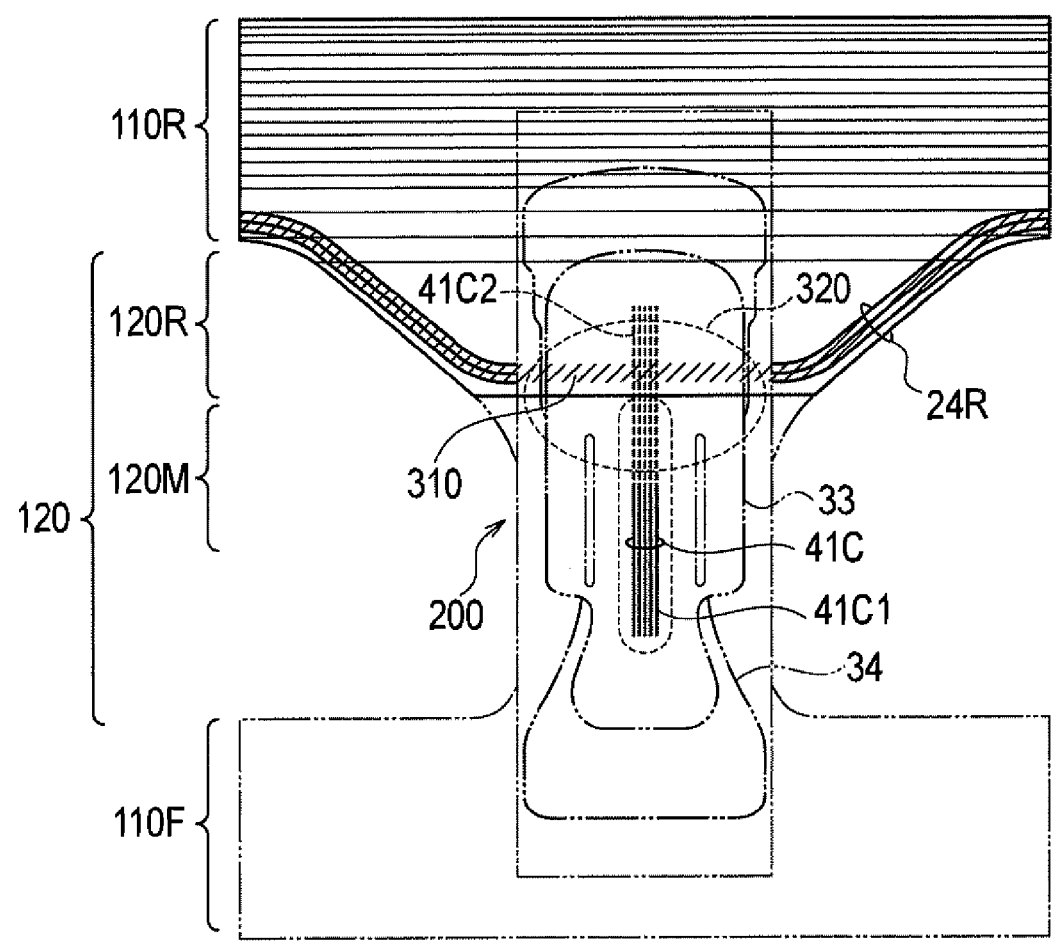
FIG. 10 is a diagram for explaining Pattern 5 according to a first modification.
Figure 11:
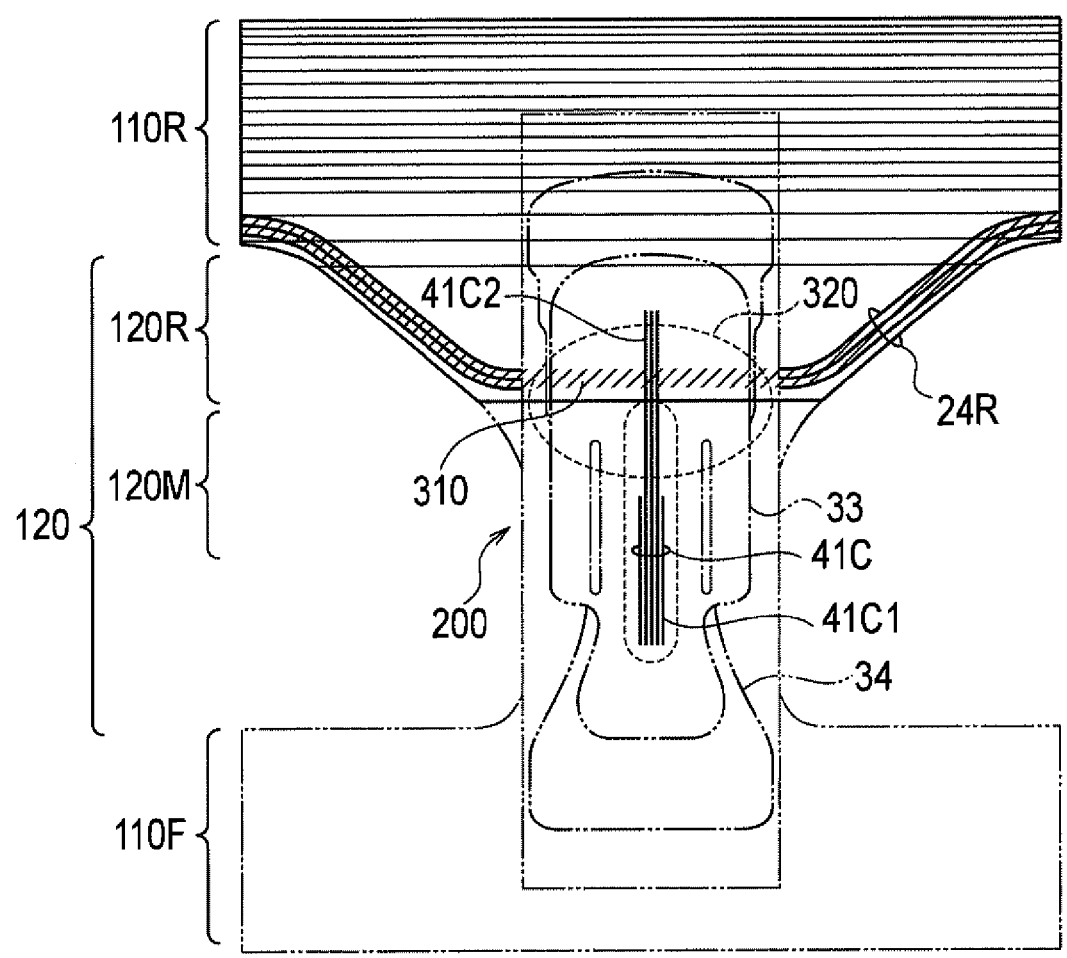
FIG. 11 is a diagram for explaining Pattern 6 according to the first modification.
Figure 12:
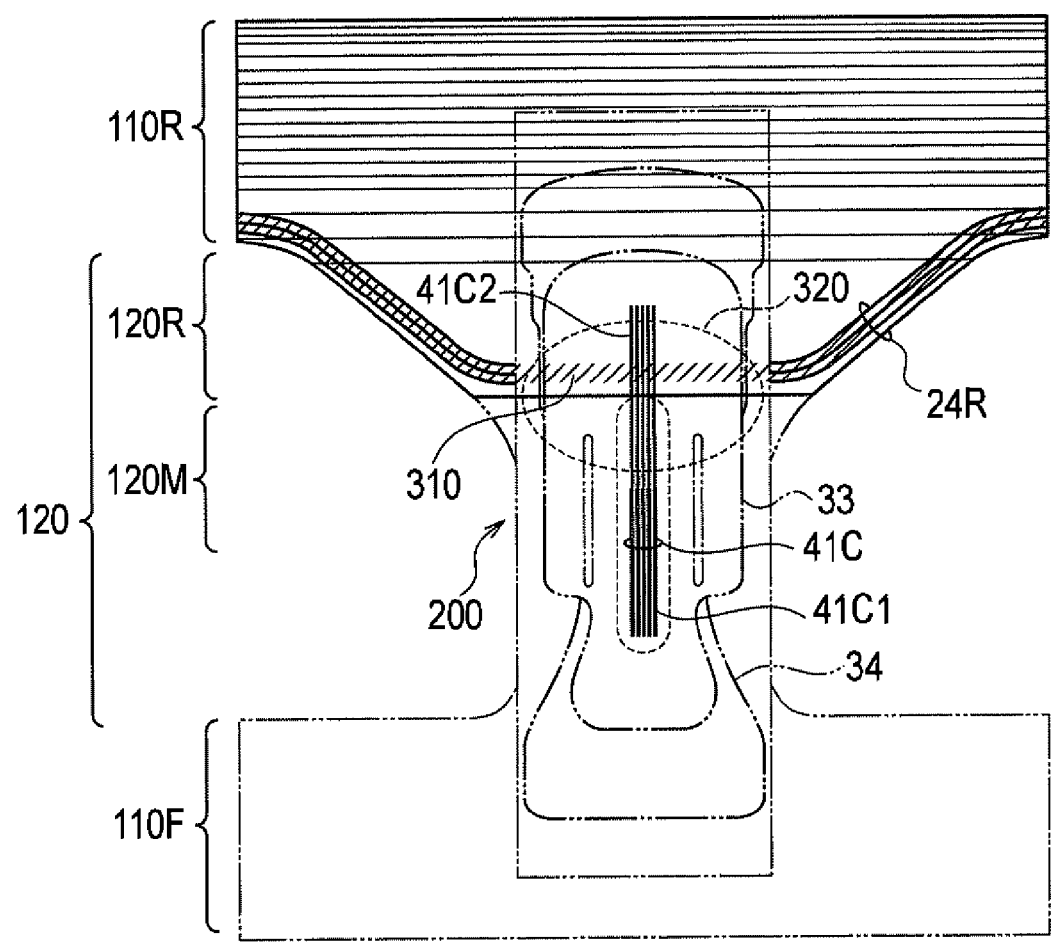
FIG. 12 is a diagram for explaining Pattern 7 according to the first modification.

As shown in FIG. 10 to FIG. 12, the wearing article 1 has the following configuration as common configuration in pattern 5 to pattern 7. Specifically, the wearing article 1 includes the back waistline region 110R and the crotch region 120. The crotch region 120 includes the region 120M (arranged to be directly under the crotch) and the middle region 120R.

The region 120M arranged to be directly under the crotch is the region that is adapted to come into contact with the crotch (for example, the area in the vicinity of the excretion portion in females) of the wearer where the width between the two legs when the wearer closes both legs is the narrowest. The middle region 120R is the region intermediate the region 120M (arranged to be directly under the crotch) and the back waistline region 110R.

The above-mentioned central elastic member 41C is arranged such that it extends along the longitudinal direction L in the region 120M directly under the crotch. However, the central elastic member 41C reaches the middle region 120R.

Specifically, the central elastic member 41C includes the portion 41C1 arranged to be directly under the crotch and an extending portion 41C2. The portion 41C1 directly under the crotch is provided at an approximately center portion of the wearing article 1 in the longitudinal direction L. In other words, the portion 41C1 directly under the crotch is provided in the region 120M directly under the crotch. The extending portion 41C2 is the portion that continues in succession to the portion 41C1 in the longitudinal direction L. In other words, the extending portion 41C2 is provided in the middle region 120R.

The back leg elastic member 24R forms a part of the elastic stress line 310. The back leg elastic member 24R is discontinuous in the portion crossing the absorber on the elastic stress line 310. That is, the back leg elastic member 24R is not provided in the portion crossing the absorber on the elastic stress line 310.

Here, the elastic stress of the extending portion 41C2 is common in pattern 5 to pattern 7, and is smaller than the elastic stress of the portion 41C1 arranged to be directly under the crotch. Thus, in the portion in which the extending portion 41C2 is provided (the middle region 120R), a urine collector 320 with a relatively small elastic stress is formed.

(Pattern 5)

Hereinafter, pattern 5 is explained with reference to FIG. 10. As shown in FIG. 10, the central elastic member 41C includes the portion 41C1 directly under the crotch and the extending portion 41C2.

In pattern 5, the extending portion 41C2 is cut off intermittently. For example, in the extending portion 41C2, an intermittent perforated tear-off line is made by a cutter. Thus, the elastic stress of the extending portion 41C2 becomes smaller than the elastic stress of the portion 41C1 directly under the crotch.

Note that in pattern 5, the elastic stress of the back leg elastic member 24R is desired to be more than the elastic stress of the extending portion 41C2, and also more than the elastic stress of the portion 41C1 directly under the crotch.

(Pattern 6)

Hereinafter, pattern 6 is explained with reference to FIG. 11. As shown in FIG. 11, the central elastic member 41C includes the portion 41C1 directly under the crotch and the extending portion 41C2.

In pattern 6, the central elastic member 41C is configured by a plurality of thread-shaped elastic members. The number of thread-shaped elastic members configuring the extending portion 41C2 (for example, 3 threads) is smaller than the number of thread-shaped elastic members configuring the portion 41C1 directly under the crotch (for example, 5 threads). Thus, the elastic stress of the extending portion 41C2 is smaller than the elastic stress of the portion 41C1 directly under the crotch.

Note that in pattern 6, the elastic stress of the back leg elastic member 24R is desired to be more than the elastic stress of the extending portion 41C2, and also more than the elastic stress of the portion 41C1 directly under the crotch.
(Pattern 7)

Hereinafter, pattern 7 is explained with reference to FIG. 12. As shown in FIG. 12, the central elastic member 41C includes the portion 41C1 directly under the crotch and the extending portion 41C2.

In pattern 7, the elastic stress of the extending portion 41C2 is smaller than the elastic stress of the portion 41C1 directly under the crotch.

This may be achieved, for example, when the central elastic member 41C is arranged between the absorber backsheet 35 and the central elastic member covering sheet 42C, the elastic stresses of the portion 41C1 directly under the crotch and of the extending portion 41C2 can be changed by changing the degree of extension of the central elastic member 41C in these distinct portions. Further, or as an alternative, the portion 41C1 directly under the crotch and the extending portion 41C2 may be configured by different types of materials.

Note that in pattern 7, the elastic stress of the back leg elastic member 24R is desired to be more than the elastic stress of the extending portion 41C2, and also more than the elastic stress of the portion 41C1 directly under the crotch.

According to the first modification, the portion 41C1 arranged to be directly under the crotch in the central elastic member 41C is provided at an approximately center portion of the wearing article 1 in the longitudinal direction L. As a result, the contact between the excretion region and the absorber is improved by the portion 41C1 directly under the crotch in the central elastic member 41C. Therefore, even in cases where the urine flow is slow, the leakage of the urine outside the wearing article 1 can be prevented. Further, in the central elastic member 41C, the elastic stress of the extending portion 41C2 is smaller than the elastic stress of the portion 41C1 directly under the crotch. As a result, in the extending portion 41C2 that continues in succession to the portion 41C1 directly under the crotch (for example, in the middle region 120R) a urine collector 320 with a relatively small elastic stress is formed. Therefore, even in cases where the amount of urine discharged is large, the leakage of the urine outside the wearing article 1 can be prevented.

In pattern 5 to pattern 7, it is desired that the extending portion 41C2 overlaps the non-skin surface side of the absorber surface sheet 32. Thus, because the elastic stress of the extending portion 41C2 is inhibited due to the rigidity of the absorber topsheet 32, the urine collector 320 is formed easily.

Also, if the extending portion 41C2, which continues in succession to the portion 41C1 directly under the crotch, is provided, excessive sagging of the wearing article 1 when the absorber becomes heavy due to absorption of urine in the absorber that overlaps the extending portion 41C2 can be prevented.

[Manufacturing Method]

Figure 13:
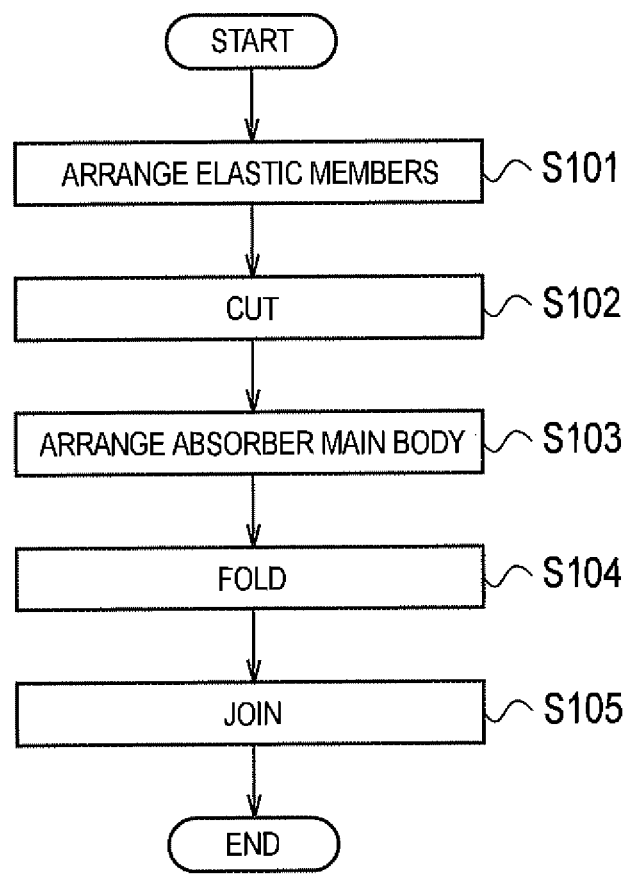
FIG. 13 is a flowchart for explaining a manufacturing method.

Hereinafter, some of the manufacturing methods of the wearing article 1 according to the embodiment are illustrated with reference to drawings. FIG. 13 is a flowchart showing a part of the manufacturing method of the wearing article 1 according to the embodiment. Note that as far as the methods that are not described in FIG. 13 are concerned, the existing methods can be used.

As shown in FIG. 13, in step S101, the elastic members for forming the front waist elastic member 23F and the front leg elastic member 24F are arranged between the sheet member for forming the exterior topsheet 21 and the sheet member for forming the front exterior backsheet 22F. Further, the elastic members for forming the back waist elastic member 23R and the back leg elastic member 24R are arranged between the sheet member for forming the exterior topsheet 21 and the sheet member for forming the back exterior backsheet 22R.

In step S102, a middle member, wherein an elastic member is arranged between the sheet members, is cut in accordance with the shape of the exterior topsheet 21, the front exterior backsheet 22F, and the back exterior backsheet 22R.

In step S103, the absorber main body 200 is arranged at a predetermined position in the middle member that is cut in step S102.

In step S104, the middle member in which the absorber main body 200 is arranged in step S103 is folded.

In step S105, the middle member that is folded in step S104 is joined. Specifically, the portion corresponding to both ends 111F of the front waistline region 110F and the portion corresponding to both ends 111R of the back waistline region 110R are joined together.

Here, one method for changing the elastic stress of the back leg elastic member 24R is explained with reference to drawings. That is, the details of the processing of step S101 are explained.

Figure 14:
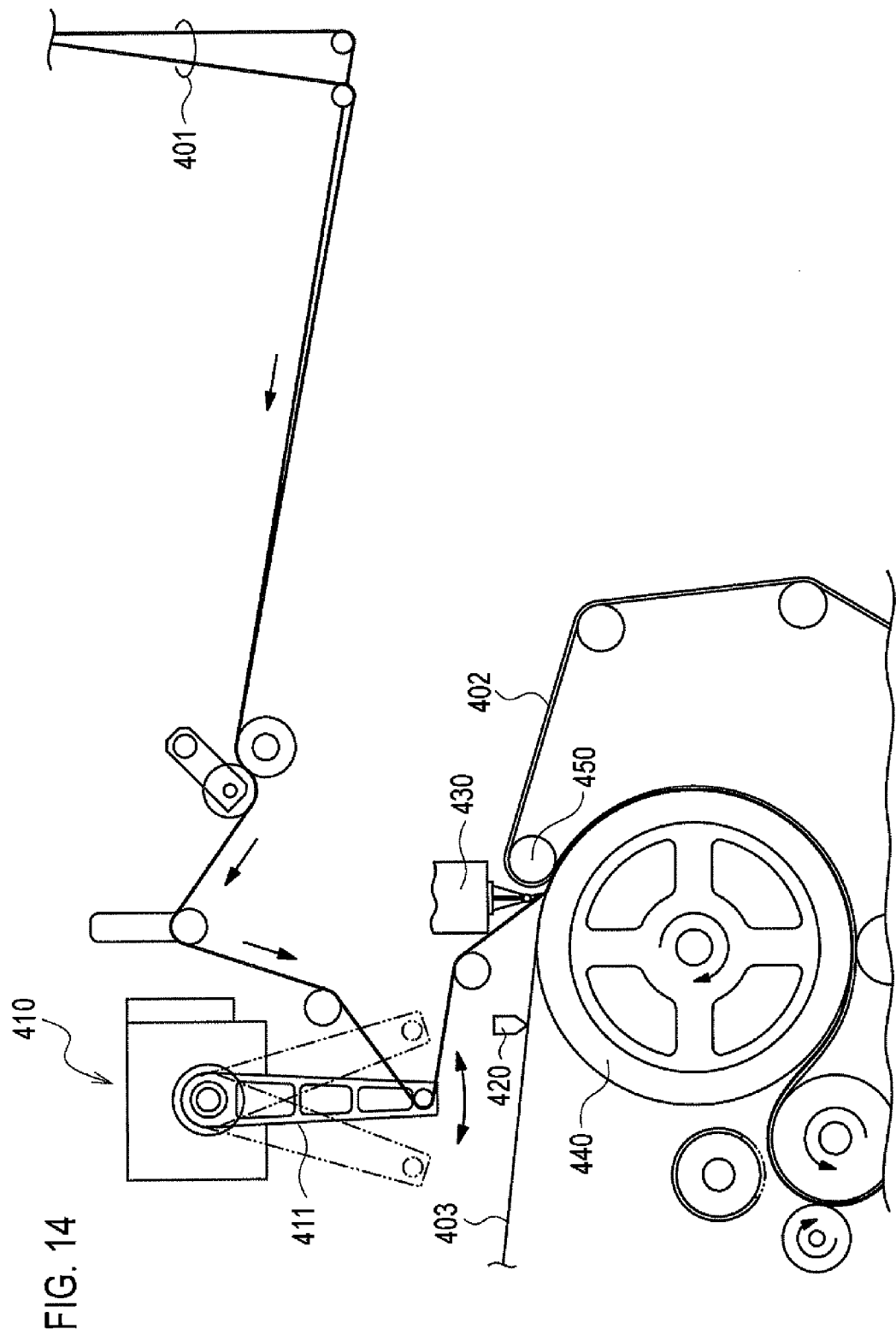
FIG. 14 is a diagram for explaining the manufacturing method.

First of all, the first method is explained with reference to FIG. 14. As shown in FIG. 14, the elastic member 401 for forming the back leg elastic member 24R is locked to the roller provided at the tip of the arm 411 of the extension rate changing device 410 by various rollers. Furthermore, the elastic member 401 is guided by the conveyance roller 440 after being adjusted to a predetermined position by a traverse device 430. On the other hand, an adhesive (for example, a hot-melt adhesive) is coated on the sheet member 402 for forming the back exterior backsheet 22R by a coating device 420 through various rollers, and is guided by the conveyance roller 440. Further, the sheet member 403 for forming the exterior topsheet 21 is also guided by the conveyance roller 440. The elastic member 401, the sheet member 402, and the sheet member 403 are guided such that they pass between the conveyance roller 440 and the pressing roller 450, and the elastic member 401 is bonded between the sheet member 402 and the sheet member 403.

Here, the extension rate changing device 410 supports the arm 411 such that it can be turned, and the extension rate of the elastic member 401 is changed by the turning of the arm 411. Note that the elastic member 401 for forming the front waist elastic member 23F, the back waist elastic member 23R, and the front leg elastic member 24F is also bonded between the sheet member 402 and the sheet member 403.

Secondly, the second method is explained with reference to FIG. 15. Note that in FIG. 15, the same symbols have been used for the configuration that is the same as in FIG. 14.

Figure 15:
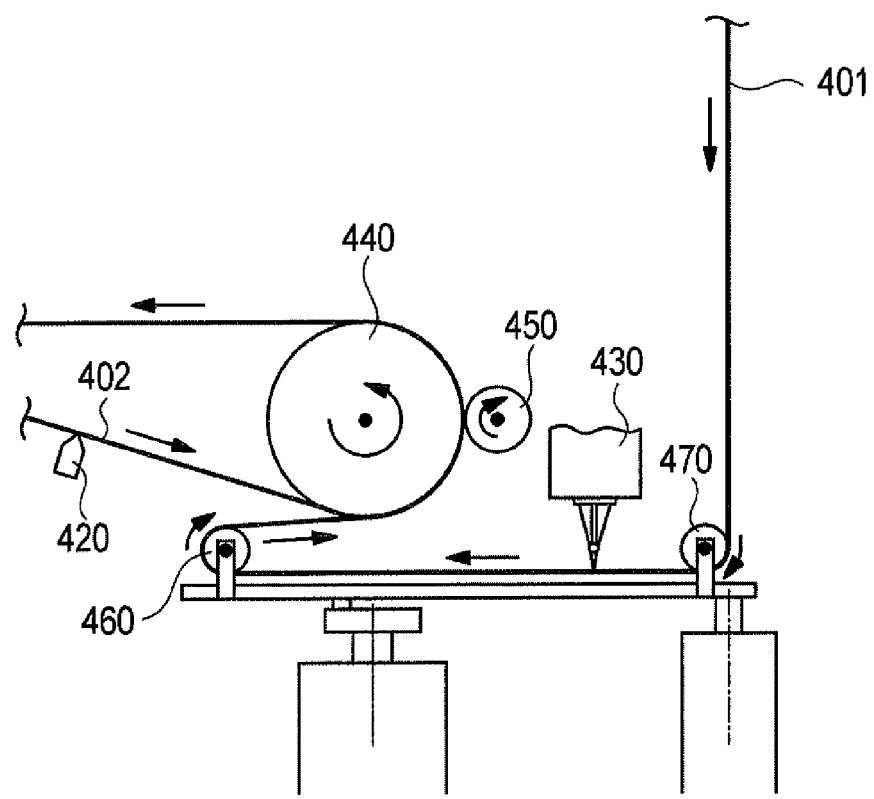
FIG. 15 is a diagram for explaining the manufacturing method.

As shown in FIG. 15, same as in the first method, the elastic member 401 and the sheet member 402 are guided by various rollers such that they pass between the conveyance roller 440 and the pressing roller 450, and the elastic member 401 is bonded to the sheet member 402.

Here, in the second method, the extension rate of the elastic member 401 is changed by controlling the conveyance velocity of the elastic member 401 by the roller 460 or the roller 470.

As regards the central elastic member 41C, note that a device such as that explained above for the leg elastic member 24R can be used for changing the elastic stress, and the central elastic member 41C can be arranged in a straight line by excluding the traverse device. To arrange the central elastic member 41C between the absorber backsheet 35 and the central elastic member covering sheet 42C, the elastic stress of the central elastic member 41C is adjusted with the above-mentioned method, and then an HMA adhesive is coated directly by using a coating method such as the slit nozzle method, it is bonded to the central elastic member covering sheet, merged with the absorber backsheet and sandwiched to be pressed and bonded such that the central elastic member 41C is bonded between the central elastic member covering sheet 42C and the absorber backsheet. At this point, by intermittently coating an HMA, the central elastic member is set and fixed at the predetermined length, and when the absorber main body is cut off at the predetermined length, the central elastic member 41C snaps back, the HMA non-coated portion returns to the above-mentioned predetermined length, and the central elastic member is fixed between the central elastic member covering sheet and the absorber backsheet at the predetermined length.

Other Embodiment

The present invention is explained through the above embodiment, but it must not be assumed that this invention is limited by the statements and drawings constituting a part of this disclosure. A variety of alternative forms of execution, embodiments, and operation techniques may become clear to those skilled in the art through this disclosure.

In the above embodiment, the chassis 100 is configured mainly by the exterior topsheet 21, the front exterior backsheet 22F, and the back exterior backsheet 22R. However, the chassis 100 is not limited thereto. For example, the chassis 100 may be of a type wherein all portions are configured by a pair of sheets (all-in type). Alternatively, the chassis 100 may be of a type in which the exterior bodies do not exist at the non-skin surface side of the absorber.

In the above embodiment, the absorber provided in the absorber main body 200 is configured by the first absorber layer 33 and the second absorber layer 34. However, the embodiment is not limited thereto. For example, the absorber may be configured by a single absorber layer.

In the above embodiment, pattern 1 to pattern 4 and pattern 5 to pattern 7 have been explained separately to clarify the description. However, the embodiment is not limited to pattern 1 to pattern 7. For example, any one of pattern 2 to pattern 4 and any one of pattern 5 to pattern 7 may even be combined together.

In the above embodiment, the back leg elastic member 24R is illustrated as the second elastic member forming at least a part of the elastic stress line 310. However, the embodiment is not limited thereto. For example, the second elastic member may even be the back waist elastic member 23R.

In the above embodiment, the back leg elastic member 24R that is provided in the back waistline region 110R is illustrated as the second elastic member. However, the embodiment is not limited thereto. For example, the second elastic member may even be the front leg elastic member 24F that is provided in the front waistline region 110F. Alternatively, the second elastic member may even be the front waist elastic member 23F that is provided in the front waistline region 110F.

For example, in cases where the second elastic member is provided in the front waistline region 110F, the urine collector 320 is formed in the lower side when the wearer is lying face down. Further, if the wearer is a male, the urine collector 320 will be formed around the excretion region. In other words, in such a case, the urine collector 320 is formed at the appropriate position.

Note that as described in the above embodiment, in cases where the second elastic member is provided in the back waistline region 110R, the urine collector 320 is formed in the lower side when the wearer is lying face up. In other words, the urine collector 320 is formed at the appropriate position.

In the above embodiment, the central elastic member 41C is illustrated as the first elastic member extending along the longitudinal direction L at an approximate center of the widthwise direction W. However, the embodiment is not limited thereto. The first elastic member may even be a panel-shaped elastic member. This may extend along the longitudinal direction L in the entire absorber in the widthwise direction W.

Preferably, Spandex is used for each elastic member and the extension magnitude of the front and back waist elastic member is between 1.4 times and 4 times in normal cases. However, in the present embodiment, at the ends of the longitudinal direction of the product, the front and back waist elastic members are arranged in a 940 DTEX×3.5 times×6 arrangement, and the other waistline elastic members are arranged in a 780 DTEX×3.0 times arrangement, in the region other than the crotch region.

Further, in the present embodiment, the magnitude is different in each portion, and while the leg elastic members are arranged in a 780 DTEX×3 arrangement, the magnitude in the portions that do not cross the absorber is 3.0 times on an average. Note that the interval of the elastic members of the leg elastic members is approximately 4 mm in the portion where the elastic members are arranged in a straight line in the crotch region.

Furthermore, in the present embodiment, the central elastic members are arranged at an interval of approximately 3 mm in a 620 DTEX×1.8 times×7 arrangement, and the length of the central elastic member is 120 mm.

Note that this application claims the benefit of Japanese Application No. 2010-096538 the entire disclosure of which is incorporated by reference herein.

INDUSTRIAL APPLICABILITY

According to the characteristic provided by some embodiments of the present invention, it is possible to provide a wearing article that enables prevention of leakage of urine outside the wearing article in the cases of both slow urine flow and discharge of a large amount of urine.

The invention claimed is:
1. A wearing article comprising a chassis, which has a waistline region and a crotch region, and an absorber main body, which has an absorber provided in at least the crotch region of the chassis, the wearing article further comprising:
   a first elastic member overlapping a non-skin-facing surface of the absorber in the crotch region and extending along a longitudinal direction of the wearing article at an approximately center of a widthwise direction of the wearing article; and
   a second elastic member which curves within the crotch region from both ends of the waistline region in the widthwise direction of the wearing article; and
   an elastic stress line which crosses the absorber along the widthwise direction of the wearing article;
   wherein the second elastic member forms at least a part of the elastic stress line; and
   wherein, in the elastic stress line, the elastic stress of the portion crossing the absorber is smaller than the elastic stress of the first elastic member.
2. The wearing article according to claim 1, wherein the second elastic member is disposed to curve within the crotch region from both ends of the waistline region in the widthwise direction of the wearing article and to cross the absorber along the widthwise direction of the wearing article, and in the second elastic member, the elastic stress of a portion crossing the absorber is smaller than the elastic stress of the first elastic member.

3. The wearing article according to claim 2, wherein in the second elastic member, the elastic stress of portions other than the portion crossing the absorber is larger than the elastic stress of the portion crossing the absorber and larger than the elastic stress of the first elastic member.

4. The wearing article according to claim 1, wherein the first elastic member and the second elastic member are disposed not to cross each other.

5. The wearing article according to claim 1, wherein the second elastic member is discontinuous in a portion crossing the absorber.

6. The wearing article according to claim 1, wherein the waistline region includes a front waistline region and a back waistline region, and the second elastic member curves within the crotch region from both ends of the back waistline region in the widthwise direction of the wearing article and configures at least a part of the elastic stress line that crosses the absorber along the widthwise direction of the wearing article.

7. The wearing article according to claim 1, wherein an interval of a plurality of first thread-shaped elastic members configuring the first elastic member is smaller than an interval of a plurality of second thread-shaped elastic members configuring the portion that crosses the absorber in the second elastic member.

8. The wearing article according to claim 1, wherein the second elastic member is positioned closer to the non-skin-facing surface of the wearing article than the first elastic member is.

9. A wearing article comprising a chassis, which has a waistline region and a crotch region, and an absorber main body, which has an absorber provided in at least the crotch region of the chassis, the wearing article further comprising:

a first elastic member overlapping the absorber in the crotch region and extending along a longitudinal direction of the wearing article at an approximate center of a widthwise direction of the wearing article, wherein the first elastic member comprises a portion arranged to be directly under the crotch of a wearer in use and provided at an approximate center of the wearing article in the longitudinal direction of the wearing article;

the first elastic member further comprises an extending portion that continues in succession to the portion arranged to be directly under the crotch in the longitudinal direction of the wearing article, and the elastic stress of the extending portion is smaller than the elastic stress of the portion arranged to be directly under the crotch.

10. The wearing article according to claim 9, further comprising a second elastic member disposed to curve within the crotch region from both ends of the waistline region in the widthwise direction of the wearing article and to cross the absorber along the widthwise direction of the wearing article, wherein in the second elastic member, the elastic stress of a portion crossing the absorber is smaller than the elastic stress of the first elastic member.

11. The wearing article according to claim 9, further comprising a second elastic member which curves within the crotch region from both ends of the waistline region in the widthwise direction of the wearing article and forms at least a part of an elastic stress line that crosses the absorber along the widthwise direction of the wearing article, wherein the second elastic member is discontinuous in a portion crossing the absorber.

* * * * *